United States Patent
Miller et al.

(10) Patent No.: US 9,492,326 B2
(45) Date of Patent: Nov. 15, 2016

(54) REDUCED PRESSURE WOUND TREATMENT SYSTEM

(71) Applicant: BlueSky Medical Group Incorporated, Memphis, TN (US)

(72) Inventors: Michael Seth Miller, Linton, IN (US); Richard Scott Weston, Encinitas, CA (US); Timothy Robert Johnson, Ocean Beach, CA (US)

(73) Assignee: BlueSky Medical Group Incorporated, Memphis, TN (US)

( * ) Notice: Subject to any disclaimer, the term of this patent is extended or adjusted under 35 U.S.C. 154(b) by 727 days.

(21) Appl. No.: 13/889,300

(22) Filed: May 7, 2013

(65) Prior Publication Data

US 2014/0012214 A1    Jan. 9, 2014

Related U.S. Application Data

(60) Division of application No. 12/856,460, filed on Aug. 13, 2010, now Pat. No. 8,540,699, which is a continuation of application No. 11/095,859, filed on Mar. 31, 2005, now Pat. No. 7,776,028.

(60) Provisional application No. 60/559,726, filed on Apr. 5, 2004.

(51) Int. Cl.
*A61M 27/00* (2006.01)
*A61F 13/00* (2006.01)
(Continued)

(52) U.S. Cl.
CPC ..... *A61F 13/00068* (2013.01); *A61F 13/0216* (2013.01); *A61M 1/0031* (2013.01);
(Continued)

(58) Field of Classification Search
CPC .................. A61M 1/0011; A61M 1/0094
USPC ......... 604/313, 315–316, 541, 543, 305, 27, 604/75–76; 602/1
See application file for complete search history.

(56) References Cited

U.S. PATENT DOCUMENTS

| 70,088 A | 10/1867 | Hadfield |
| 774,529 A | 11/1904 | Nieschange |

(Continued)

FOREIGN PATENT DOCUMENTS

| CA | 2198243 A1 | 2/1996 |
| CA | 2238413 A1 | 5/1997 |

(Continued)

OTHER PUBLICATIONS

U.S. Appl. No. 10/599,720, filed Oct. 6, 2006, Blott et al.

(Continued)

*Primary Examiner* — Paula L. Craig
(74) *Attorney, Agent, or Firm* — Knobbe, Martens, Olson & Bear LLP

(57) ABSTRACT

A reduced pressure treatment appliance is provided for treating a wound on the body of a patient. In some embodiments, the appliance comprises an overlay, which is further comprised of cup members that may be detached or cut away from the overlay so that the overlay can be adjusted in size and shape. Also, in some embodiments, the overlay is further comprised of a pressure venting valve to maintain a predetermined level of reduced pressure at the site of the wound. In other embodiments, the wound treatment appliance also includes a vacuum system to supply reduced pressure to the site of the wound in the volume under the overlay. In yet other embodiments, the treatment appliance also includes wound packing means to prevent overgrowth of the wound or to encourage growth of wound tissue into an absorbable matrix comprising the wound packing means. In still other embodiments, a suction bulb may be used to provide a source of reduced pressure to an overlay that covers the wound. Finally, methods are provided for using various embodiments of the treatment appliance.

13 Claims, 5 Drawing Sheets

(51) Int. Cl.
*A61F 13/02* (2006.01)
*A61M 1/00* (2006.01)
(52) U.S. Cl.
CPC ......... *A61M1/0072* (2014.02); *A61M 1/0088* (2013.01); *A61M 1/0092* (2014.02); *A61M 27/00* (2013.01); *A61F 2013/00089* (2013.01); *A61F 2013/00217* (2013.01); *A61M 1/0003* (2013.01)

(56) References Cited

U.S. PATENT DOCUMENTS

| | | | |
|---|---|---|---|
| 1,480,562 A | 1/1924 | Mock | |
| 1,585,104 A | 5/1926 | Montgomery | |
| 1,732,310 A | 12/1929 | Naibert | |
| 1,863,534 A | 6/1932 | Odell | |
| 1,936,129 A | 11/1933 | Fisk | |
| 2,122,121 A | 6/1938 | Tillotson | |
| 2,195,771 A | 4/1940 | Estler | |
| 2,280,915 A | 4/1942 | Johnson | |
| 2,367,690 A | 7/1943 | Purdy | |
| 2,366,799 A | 1/1945 | Luisada | |
| 2,568,933 A | 9/1951 | Robbins | |
| 2,632,443 A | 3/1953 | Lesher | |
| 2,682,873 A | 7/1954 | Evans et al. | |
| 3,026,874 A | 11/1959 | Stevens | |
| 2,927,577 A | 3/1960 | Nicolaie | |
| 3,042,041 A | 7/1962 | Jascalevich | |
| 3,123,074 A | 3/1964 | Turner | |
| 3,217,707 A | 11/1965 | Werding | |
| 3,238,937 A | 3/1966 | Stein | |
| 3,286,711 A | 11/1966 | MacLeod | |
| 3,315,665 A | 4/1967 | MacLeod | |
| 3,367,332 A | 2/1968 | Groves | |
| 3,376,868 A * | 4/1968 | Mondiadis ........... | A61M 1/0011 417/472 |
| 3,465,748 A | 9/1969 | Kravchenko | |
| 3,486,504 A | 12/1969 | Austin, Jr. | |
| 3,568,675 A | 3/1971 | Harvey | |
| 3,572,340 A | 3/1971 | Lloyd et al. | |
| 3,610,238 A | 10/1971 | Rich, Jr. | |
| 3,712,298 A | 1/1973 | Snowdon et al. | |
| 3,794,035 A | 2/1974 | Brenner | |
| 3,859,989 A | 1/1975 | Spielberg | |
| 3,874,387 A | 4/1975 | Barbieri | |
| 3,938,540 A | 2/1976 | Holbrook et al. | |
| 3,961,625 A | 6/1976 | Dillon | |
| 3,988,793 A | 11/1976 | Abitbol | |
| 3,993,080 A | 11/1976 | Loseff | |
| RE29,319 E | 7/1977 | Nordby et al. | |
| 4,080,970 A | 3/1978 | Miller | |
| 4,102,342 A | 7/1978 | Akiyama et al. | |
| 4,112,947 A | 9/1978 | Nehring | |
| 4,136,696 A | 1/1979 | Nehring | |
| 4,184,510 A | 1/1980 | Murry et al. | |
| 4,217,894 A | 8/1980 | Franetzki | |
| 4,219,019 A | 8/1980 | Coates | |
| 4,224,945 A | 9/1980 | Cohen | |
| 4,250,882 A | 2/1981 | Adair | |
| 4,256,109 A | 3/1981 | Nichols | |
| 4,316,466 A | 2/1982 | Babb | |
| 4,382,441 A | 5/1983 | Svedman | |
| 4,444,548 A | 4/1984 | Andersen et al. | |
| 4,459,139 A | 7/1984 | vonReis et al. | |
| 4,465,485 A | 8/1984 | Kashmer et al. | |
| 4,468,227 A | 8/1984 | Jensen | |
| 4,525,166 A | 6/1985 | Leclerc | |
| 4,534,356 A | 8/1985 | Papadakis | |
| 4,551,141 A | 11/1985 | McNeil | |
| 4,573,965 A | 3/1986 | Russo | |
| 4,608,041 A | 8/1986 | Nielsen | |
| 4,655,766 A | 4/1987 | Theeuwes et al. | |
| 4,691,695 A | 9/1987 | Birk et al. | |
| 4,710,165 A | 12/1987 | McNeil et al. | |
| 4,738,249 A | 4/1988 | Linman et al. | |
| 4,753,231 A | 6/1988 | Lang et al. | |
| 4,778,446 A | 10/1988 | Jensen | |
| 4,778,456 A | 10/1988 | Lokken | |
| 4,792,328 A | 12/1988 | Beck et al. | |
| 4,795,435 A | 1/1989 | Steer | |
| 4,820,284 A | 4/1989 | Hauri | |
| 4,841,962 A | 6/1989 | Berg et al. | |
| 4,847,083 A | 7/1989 | Clark | |
| 4,921,488 A | 5/1990 | Maitz et al. | |
| 4,936,834 A | 6/1990 | Beck et al. | |
| 4,950,483 A | 8/1990 | Ksander et al. | |
| 4,969,880 A | 11/1990 | Zamierowski | |
| 4,972,829 A | 11/1990 | Knerr | |
| 4,979,944 A | 12/1990 | Luzsicza | |
| 5,055,198 A | 10/1991 | Shettigar | |
| 5,056,510 A | 10/1991 | Gilman | |
| 5,073,172 A | 12/1991 | Fell | |
| 5,100,396 A | 3/1992 | Zamierowski | |
| 5,149,331 A | 9/1992 | Ferdman et al. | |
| 5,152,757 A | 10/1992 | Eriksson | |
| 5,167,613 A | 12/1992 | Karami et al. | |
| 5,176,663 A | 1/1993 | Svedman et al. | |
| 5,228,431 A | 7/1993 | Giarretto | |
| 5,261,893 A | 11/1993 | Zamierowski | |
| 5,264,218 A | 11/1993 | Rogozinski | |
| 5,266,928 A | 11/1993 | Johnson | |
| 5,279,608 A | 1/1994 | Cherif Cheikh | |
| 5,328,614 A | 7/1994 | Matsumura | |
| 5,358,494 A | 10/1994 | Svedman | |
| 5,362,543 A | 11/1994 | Nickerson | |
| 5,380,280 A | 1/1995 | Peterson | |
| 5,437,651 A | 8/1995 | Todd et al. | |
| 5,445,604 A | 8/1995 | Lang | |
| 5,462,514 A | 10/1995 | Harris | |
| 5,489,280 A | 2/1996 | Russell | |
| 5,498,338 A | 3/1996 | Kruger et al. | |
| 5,527,293 A | 6/1996 | Zamierowski | |
| 5,549,584 A | 8/1996 | Gross | |
| 5,563,233 A | 10/1996 | Reich et al. | |
| 5,618,556 A | 4/1997 | Johns et al. | |
| 5,636,643 A | 6/1997 | Argenta | |
| 5,643,189 A | 7/1997 | Masini | |
| 5,645,081 A | 7/1997 | Argenta | |
| 5,688,225 A | 11/1997 | Walker | |
| 5,701,917 A | 12/1997 | Khouri | |
| 5,716,411 A | 2/1998 | Orgill et al. | |
| 5,759,570 A | 6/1998 | Arnold | |
| 5,785,688 A | 7/1998 | Joshi et al. | |
| 5,827,246 A | 10/1998 | Bowen | |
| 5,830,496 A | 11/1998 | Freeman | |
| 5,833,646 A | 11/1998 | Masini | |
| 5,857,502 A | 1/1999 | Buchalter | |
| 5,868,933 A | 2/1999 | Patrick et al. | |
| 5,876,387 A | 3/1999 | Killian et al. | |
| 5,885,237 A | 3/1999 | Kadash | |
| 5,893,368 A | 4/1999 | Sugerman | |
| 5,938,626 A | 8/1999 | Sugerman | |
| 5,964,723 A | 10/1999 | Augustine | |
| 5,970,266 A | 10/1999 | Takato | |
| 6,045,541 A | 4/2000 | Matsumoto et al. | |
| 6,071,267 A | 6/2000 | Zamierowski | |
| 6,110,197 A | 8/2000 | Augustine et al. | |
| 6,113,548 A | 9/2000 | deBoisblanc et al. | |
| 6,135,116 A | 10/2000 | Vogel et al. | |
| D434,150 S | 11/2000 | Tumey et al. | |
| 6,142,982 A | 11/2000 | Hunt et al. | |
| 6,168,800 B1 | 1/2001 | Dobos et al. | |
| 6,176,307 B1 | 1/2001 | Danos et al. | |
| 6,200,596 B1 | 3/2001 | Schwartzmiller et al. | |
| 6,225,523 B1 | 5/2001 | Masini | |
| 6,254,567 B1 | 7/2001 | Treu et al. | |
| 6,255,552 B1 | 7/2001 | Cummings et al. | |
| 6,287,521 B1 | 9/2001 | Quay et al. | |
| 6,345,623 B1 | 2/2002 | Heaton et al. | |
| 6,371,976 B1 | 4/2002 | Vrzalik et al. | |
| 6,398,767 B1 | 6/2002 | Fleischmann | |
| 6,402,724 B1 | 6/2002 | Smith et al. | |
| 6,450,773 B1 | 9/2002 | Upton | |
| 6,458,109 B1 | 10/2002 | Henley et al. | |

(56) References Cited

U.S. PATENT DOCUMENTS

| | | |
|---|---|---|
| 6,465,708 B1 | 10/2002 | Augustine |
| 6,471,685 B1 | 10/2002 | Johnson |
| 6,471,982 B1 | 10/2002 | Lydon et al. |
| 6,482,491 B1 | 11/2002 | Samuelsen et al. |
| 6,491,684 B1 | 12/2002 | Joshi et al. |
| 6,509,391 B2 | 1/2003 | Gothjaelpsen et al. |
| 6,553,998 B2 | 4/2003 | Heaton et al. |
| 6,566,833 B2 | 5/2003 | Bartlett |
| 6,571,825 B2 | 6/2003 | Stacy |
| 6,595,949 B1 | 7/2003 | Shapiro |
| 6,599,262 B1 | 7/2003 | Masini |
| 6,648,862 B2 | 11/2003 | Watson |
| 6,673,028 B1 | 1/2004 | Argenta et al. |
| 6,676,610 B2 | 1/2004 | Morton et al. |
| 6,682,506 B1 | 1/2004 | Navarro |
| 6,685,681 B2 | 2/2004 | Lockwood et al. |
| 6,695,823 B1 | 2/2004 | Lina et al. |
| 6,695,824 B2 | 2/2004 | Howard et al. |
| 6,752,794 B2 | 6/2004 | Lockwood et al. |
| 6,755,807 B2 | 6/2004 | Risk et al. |
| 6,764,462 B2 | 7/2004 | Risk, Jr. et al. |
| 6,767,334 B1 | 7/2004 | Randolph |
| 6,787,682 B2 | 9/2004 | Gilman |
| 6,800,074 B2 | 10/2004 | Henley et al. |
| 6,814,079 B2 | 11/2004 | Heaton et al. |
| 6,824,533 B2 | 11/2004 | Risk, Jr. et al. |
| 6,855,135 B2 | 2/2005 | Lockwood et al. |
| 6,856,821 B2 | 2/2005 | Johnson |
| 6,904,631 B2 | 6/2005 | Vrzalik et al. |
| 6,936,037 B2 | 8/2005 | Bubb et al. |
| 6,951,553 B2 | 10/2005 | Bubb et al. |
| 6,977,323 B1 | 12/2005 | Swenson |
| 6,979,324 B2 | 12/2005 | Bybordi et al. |
| 6,988,423 B2 | 1/2006 | Bolam et al. |
| 6,994,702 B1 | 2/2006 | Johnson |
| 7,004,915 B2 | 2/2006 | Boynton et al. |
| 7,022,113 B2 | 4/2006 | Lockwood et al. |
| 7,070,584 B2 | 7/2006 | Johnson et al. |
| 7,077,832 B2 | 7/2006 | Fleischmann |
| 7,108,683 B2 | 9/2006 | Zamierowski |
| 7,117,869 B2 | 10/2006 | Heaton et al. |
| 7,118,545 B2 | 10/2006 | Boyde |
| 7,128,735 B2 | 10/2006 | Weston |
| 7,144,390 B1 | 12/2006 | Hannigan et al. |
| 7,195,624 B2 | 3/2007 | Lockwood |
| 7,216,651 B2 | 5/2007 | Argenta et al. |
| 7,279,612 B1 | 10/2007 | Heaton et al. |
| 7,361,184 B2 | 4/2008 | Joshi |
| 7,381,859 B2 | 6/2008 | Hunt et al. |
| 7,438,705 B2 | 10/2008 | Karpowicz et al. |
| 7,470,830 B2 | 12/2008 | Sigurjonsson et al. |
| 7,494,482 B2 | 2/2009 | Orgill et al. |
| 7,507,870 B2 | 3/2009 | Nielsen et al. |
| 7,524,286 B2 | 4/2009 | Johnson |
| 7,524,315 B2 | 4/2009 | Blott et al. |
| 7,534,240 B1 | 5/2009 | Johnson |
| 7,534,927 B2 | 5/2009 | Lockwood et al. |
| 7,553,306 B1 | 6/2009 | Hunt et al. |
| 7,569,742 B2 | 8/2009 | Haggstrom et al. |
| 7,611,500 B1 | 11/2009 | Lina et al. |
| 7,612,247 B2 | 11/2009 | Oyaski |
| 7,615,036 B2 | 11/2009 | Joshi et al. |
| 7,625,362 B2 | 12/2009 | Boehringer et al. |
| 7,645,269 B2 | 1/2010 | Zamierowski |
| 7,678,102 B1 | 3/2010 | Heaton |
| 7,699,830 B2 | 4/2010 | Martin |
| 7,708,724 B2 | 5/2010 | Weston |
| 7,723,560 B2 | 5/2010 | Lockwood et al. |
| 7,731,702 B2 | 6/2010 | Bybordi |
| 7,753,894 B2 | 7/2010 | Blott et al. |
| 7,759,537 B2 | 7/2010 | Bishop et al. |
| 7,759,538 B2 | 7/2010 | Fleischmann |
| 7,759,539 B2 | 7/2010 | Shaw et al. |
| 7,775,998 B2 | 8/2010 | Riesinger |
| 7,776,028 B2 | 8/2010 | Miller et al. |
| 7,779,625 B2 | 8/2010 | Joshi et al. |
| 7,790,945 B1 | 9/2010 | Watson, Jr. |
| 7,790,946 B2 | 9/2010 | Mulligan |
| 7,794,438 B2 | 9/2010 | Henley et al. |
| 7,794,450 B2 | 9/2010 | Blott et al. |
| 7,799,004 B2 | 9/2010 | Tumey |
| 7,815,616 B2 | 10/2010 | Boehringer et al. |
| 7,828,782 B2 | 11/2010 | Suzuki |
| 7,846,141 B2 | 12/2010 | Weston |
| 7,883,494 B2 | 2/2011 | Martin |
| 7,896,856 B2 | 3/2011 | Petrosenko et al. |
| 7,909,805 B2 | 3/2011 | Weston |
| 7,927,318 B2 | 4/2011 | Risk, Jr. et al. |
| 7,959,624 B2 | 6/2011 | Riesinger |
| 7,964,766 B2 | 6/2011 | Blott et al. |
| 7,976,519 B2 | 7/2011 | Bubb et al. |
| 7,998,125 B2 | 8/2011 | Weston |
| 8,012,169 B2 | 9/2011 | Joshi |
| 8,034,037 B2 | 10/2011 | Adams et al. |
| 8,062,272 B2 | 11/2011 | Weston |
| 8,062,273 B2 | 11/2011 | Weston |
| 8,080,702 B2 | 12/2011 | Blott et al. |
| 8,100,887 B2 | 1/2012 | Weston |
| 8,105,295 B2 | 1/2012 | Blott et al. |
| 8,118,794 B2 | 2/2012 | Weston |
| 8,128,615 B2 | 3/2012 | Blott |
| 8,133,211 B2 | 3/2012 | Cavanaugh, II et al. |
| 8,147,468 B2 | 4/2012 | Barta et al. |
| 8,152,785 B2 | 4/2012 | Vitaris |
| 8,162,909 B2 | 4/2012 | Blott et al. |
| 8,188,331 B2 | 5/2012 | Barta et al. |
| 8,202,261 B2 | 6/2012 | Kazala, Jr. et al. |
| 8,207,392 B2 | 6/2012 | Haggstrom et al. |
| 8,235,955 B2 | 8/2012 | Blott et al. |
| 8,241,261 B2 | 8/2012 | Randolph et al. |
| 8,257,327 B2 | 9/2012 | Blott et al. |
| 8,282,611 B2 | 10/2012 | Weston |
| 8,303,552 B2 | 11/2012 | Weston |
| 8,348,910 B2 | 1/2013 | Blott et al. |
| 8,398,614 B2 | 3/2013 | Blott et al. |
| 8,444,612 B2 | 5/2013 | Patel et al. |
| 8,449,509 B2 | 5/2013 | Weston |
| 8,460,255 B2 | 6/2013 | Joshi et al. |
| 8,535,296 B2 | 9/2013 | Blott et al. |
| 8,540,699 B2 | 9/2013 | Miller et al. |
| 8,545,464 B2 | 10/2013 | Weston |
| 8,569,566 B2 | 10/2013 | Blott et al. |
| 8,628,505 B2 | 1/2014 | Weston |
| 8,641,691 B2 | 2/2014 | Fink et al. |
| 8,663,198 B2 | 3/2014 | Buan et al. |
| 8,708,998 B2 | 4/2014 | Weston et al. |
| 8,715,256 B2 | 5/2014 | Greener |
| 8,764,732 B2 | 7/2014 | Hartwell |
| 8,784,393 B2 | 7/2014 | Weston et al. |
| 8,795,243 B2 | 8/2014 | Weston |
| 8,808,274 B2 | 8/2014 | Hartwell |
| 8,905,985 B2 | 12/2014 | Allen et al. |
| 9,198,801 B2 | 12/2015 | Weston |
| 9,272,080 B2 | 3/2016 | Weston |
| 2001/0029956 A1* | 10/2001 | Argenta ............ A61F 13/00068 128/897 |
| 2001/0034499 A1 | 10/2001 | Sessions et al. |
| 2002/0065494 A1* | 5/2002 | Lockwood ........... A61M 1/0058 604/313 |
| 2002/0068913 A1 | 6/2002 | Fleischmann |
| 2002/0115952 A1 | 8/2002 | Johnson |
| 2002/0143286 A1 | 10/2002 | Tumey |
| 2002/0161346 A1 | 10/2002 | Lockwood et al. |
| 2002/0183702 A1 | 12/2002 | Henley et al. |
| 2003/0014025 A1 | 1/2003 | Allen et al. |
| 2003/0021775 A1 | 1/2003 | Freeman |
| 2003/0040687 A1 | 2/2003 | Boynton et al. |
| 2003/0050594 A1 | 3/2003 | Zamierowski |
| 2003/0108587 A1 | 6/2003 | Orgill et al. |
| 2003/0125646 A1 | 7/2003 | Whitlock |
| 2003/0144619 A1 | 7/2003 | Augustine |
| 2003/0171675 A1 | 9/2003 | Rosenberg |
| 2003/0175798 A1 | 9/2003 | Raees et al. |
| 2003/0212357 A1 | 11/2003 | Pace |

(56) References Cited

U.S. PATENT DOCUMENTS

| | | |
|---|---|---|
| 2003/0212431 A1 | 11/2003 | Brady et al. |
| 2003/0225347 A1 | 12/2003 | Argenta et al. |
| 2004/0019342 A1 | 1/2004 | Nagasuna et al. |
| 2004/0039391 A1 | 2/2004 | Argenta et al. |
| 2004/0064132 A1 | 4/2004 | Boehringer et al. |
| 2004/0122434 A1 | 6/2004 | Argenta et al. |
| 2004/0241214 A1 | 12/2004 | Kirkwood et al. |
| 2006/0029650 A1 | 2/2006 | Coffey |
| 2007/0038172 A1 | 2/2007 | Zamierowski |
| 2007/0185463 A1 | 8/2007 | Mulligan |
| 2007/0239139 A1 | 10/2007 | Weston et al. |
| 2008/0132819 A1 | 6/2008 | Radl et al. |
| 2008/0167593 A1 | 7/2008 | Fleischmann |
| 2008/0188820 A1 | 8/2008 | Joshi |
| 2008/0223378 A1 | 9/2008 | Henderson et al. |
| 2009/0054855 A1 | 2/2009 | Blott et al. |
| 2009/0131888 A1 | 5/2009 | Joshi |
| 2009/0216170 A1 | 8/2009 | Robinson et al. |
| 2009/0221977 A1 | 9/2009 | Blott et al. |
| 2009/0227969 A1 | 9/2009 | Jaeb et al. |
| 2009/0234309 A1 | 9/2009 | Vitaris et al. |
| 2009/0240185 A1 | 9/2009 | Jaeb et al. |
| 2009/0299251 A1 | 12/2009 | Buan |
| 2009/0299255 A1 | 12/2009 | Kazala, Jr. et al. |
| 2009/0299257 A1 | 12/2009 | Long et al. |
| 2009/0299306 A1 | 12/2009 | Buan |
| 2009/0306580 A1 | 12/2009 | Blott et al. |
| 2009/0312723 A1 | 12/2009 | Blott et al. |
| 2010/0036367 A1 | 2/2010 | Krohn |
| 2010/0069858 A1 | 3/2010 | Olson |
| 2010/0069863 A1 | 3/2010 | Olson |
| 2010/0106114 A1 | 4/2010 | Weston et al. |
| 2010/0121286 A1 | 5/2010 | Locke et al. |
| 2010/0122417 A1 | 5/2010 | Vrzalik et al. |
| 2010/0125258 A1 | 5/2010 | Coulthard et al. |
| 2010/0249733 A9 | 9/2010 | Blott et al. |
| 2010/0286635 A1 | 11/2010 | Watson, Jr. |
| 2010/0305490 A1 | 12/2010 | Coulthard et al. |
| 2010/0324510 A1 | 12/2010 | Andresen et al. |
| 2011/0004172 A1 | 1/2011 | Eckstein et al. |
| 2011/0009835 A1 | 1/2011 | Blott et al. |
| 2011/0034892 A1 | 2/2011 | Buan |
| 2011/0054422 A1 | 3/2011 | Locke et al. |
| 2011/0054423 A1 | 3/2011 | Blott et al. |
| 2011/0087178 A2 | 4/2011 | Weston |
| 2011/0092927 A1 | 4/2011 | Wilkes et al. |
| 2011/0105963 A1 | 5/2011 | Hu et al. |
| 2011/0106030 A1 | 5/2011 | Scholz |
| 2011/0112492 A1 | 5/2011 | Bharti et al. |
| 2011/0118683 A1 | 5/2011 | Weston |
| 2011/0230849 A1 | 9/2011 | Coulthard et al. |
| 2011/0282309 A1 | 11/2011 | Adie et al. |
| 2012/0041399 A1 | 2/2012 | Blott et al. |
| 2012/0053538 A1 | 3/2012 | Blott et al. |
| 2012/0157942 A1 | 6/2012 | Weston |
| 2012/0209224 A1 | 8/2012 | Weston |
| 2013/0110058 A1 | 5/2013 | Adie et al. |

FOREIGN PATENT DOCUMENTS

| | | |
|---|---|---|
| CA | 2471780 A1 | 3/1999 |
| CA | 2432293 A1 | 2/2003 |
| CA | 2490027 A1 | 12/2003 |
| DE | 3935818 | 5/1991 |
| DE | 4012232 A1 | 10/1991 |
| DE | 19844355 | 4/2000 |
| DE | 202005019670 U1 | 12/2005 |
| EP | 0020662 B1 | 7/1984 |
| EP | 0355186 A | 2/1990 |
| EP | 0782421 | 7/1999 |
| EP | 1088 569 A | 4/2001 |
| EP | 0708620 | 5/2003 |
| EP | 1440667 | 3/2006 |
| EP | 1284777 | 4/2006 |
| EP | 1171065 | 3/2007 |
| EP | 1476217 | 3/2008 |
| EP | 1121163 | 11/2008 |
| EP | 2 098 257 | 9/2009 |
| FR | 1163907 | 5/1958 |
| GB | 114754 | 4/1918 |
| GB | 641061 | 8/1950 |
| GB | 1224009 A | 3/1971 |
| GB | 1549756 A | 8/1979 |
| GB | 2195255 A | 4/1988 |
| GB | 2378392 A | 2/2003 |
| JP | 2003-165843 | 6/2003 |
| RU | 240188 | 3/1969 |
| SU | 1251912 A1 | 8/1986 |
| WO | WO 84/01904 | 5/1984 |
| WO | WO 87/04626 | 8/1987 |
| WO | WO 91/00718 | 1/1991 |
| WO | WO 92/20299 | 11/1992 |
| WO | WO 96/05873 | 2/1996 |
| WO | WO 99/01173 | 1/1999 |
| WO | WO 00/07653 | 2/2000 |
| WO | WO 00/50143 | 8/2000 |
| WO | WO 00/59418 | 10/2000 |
| WO | WO 00/59424 | 10/2000 |
| WO | WO 01/19430 | 3/2001 |
| WO | WO 01/34223 | 5/2001 |
| WO | WO 01/85248 | 11/2001 |
| WO | WO 01/93793 | 12/2001 |
| WO | WO 02/083046 | 10/2002 |
| WO | WO 02/092783 | 11/2002 |
| WO | WO 03/073970 | 9/2003 |
| WO | WO 03/092620 | 11/2003 |
| WO | WO 2004/024300 | 3/2004 |
| WO | WO 2004/037334 | 5/2004 |
| WO | WO 2005/025666 | 3/2005 |
| WO | WO 2005/051461 | 6/2005 |
| WO | WO 2005/070480 | 8/2005 |
| WO | WO 2005/082435 | 9/2005 |

OTHER PUBLICATIONS

U.S. Appl. No. 12/192,000, filed Apr. 14, 2008, Hartwell.
U.S. Appl. No. 12/192,000, filed Aug. 14, 2008, Hartwell et al.
Achterberg et al., "Hydroactive dressings and serum proteins: an in vitro study," Journal of Wound Care, vol. 5, No. 2, Feb. 1996 (pp. 79-82).
Argenta, Louis C., et al., "Vacuum-Assisted Closure: A New Method for Wound Control and Treatment; Clinical Experience", Ann Plas Surg 1997;38:563-577 (Dec. 10, 1996).
Bagautdinov, N.A. "Variant of External Vacuum Aspiration in the Treatment of Purulent Diseases of Soft Tissues," in Current Problems in Modern Clinical Surgery: Interdepartmental Collection, edited by V.Ye. Volkov et al. (Chuvashia State University, Cheboksary, USSR 1986) pp. 94-96.
Chintamani, et al., "Half versus full vacuum suction drainage after modified radical mastectomy for breast cancer—a prospective randomized clinical trial", Research Article (Jan. 27, 2005), 1-5.
Davydov et al. "Pathogenic Mechanism of the Effect of Vacuum Therapy on the Course of the Wound Process" pp. 42-47 (Dec. 1990).
Davydov, Yu A., et al., "Concepts for Clinical Biological Management of the Wound Process in the Treatment of Purulent Wounds Using Vacuum Therapy", The Kremlin Papers: Perspectives in Wound Care, Russian Journal: Vestnik Khirurgii, BlueSky Publishing, La Costa, California (2004), 15-17.
Davydov, Yu A., et al., "The Bacteriological and Cytological Assessment of Vacuum Therapy of Purulent Wounds", The Kremlin Papers: Perspectives in Wound Care, Russian Journal: Vestnik Khirurgii, BlueSky Publishing, La Costa, California (2004), 11-14.
De Lange, M.Y., et al., "Vacuum-Assisted Closure: Indications and Clinical Experience", Eur J Plast Surg (2000) 2;178-182 (Feb. 9, 2000).
Health Technology, Literature R., "Vacuum Assisted Closure Therapy for Wound Care", Health Technology Literature Review (Dec. 2004), 3-59.

(56) References Cited

OTHER PUBLICATIONS

Khirugii, Vestnik, "A Collection of Published Studies Complementing the Research and Innovation of Wound Care", The Kremlin Papers, Perspectives in Wound Care, Russian Medical Journal, Vestnik Khirugii, Blue Sky Publishing (2004), 2-17.
Kostiuchenok, B. M., et al., "The Vacuum Effect in the Surgical Treatment of Purulent Wounds", The Kremlin Papers: Perspectives in Wound Care, Russian Journal: Vestnik Khirurgii, BlueSky Publishing, La Costa, California (2004), 3-4.
Morykwas, Michael J., et al., "Vacuum-Assisted Closure: A New Method for Wound Control and Treatment: Animal Studies and Basic Foundation", Ann Plast Surg 1997;38:553-562 (Dec. 10, 1996).
Solovev et al., "The Method of Treatment of Immature External Fistulas in the Upper Gastrointestinal Tract," USSR Ministry of Health, S.M. Kirov Gorky State Medical Institute, 1987. (with English translation).
Solovev, V.A. "Treatment and Prevention of Suture Failures after Gastric Resection" (Dissertation Abstract) (S.M. Kirov Gorky State Medical Institute, Gorky USSR 1988).
Stewart, Joanne, "Next generation products for wound management," http://www.worldwidewounds.com/2003/april/Stewart/Next-Generation-Products.html, Nov. 2002.
Svedman, "Irrigation Treatment of Leg Ulcers," The Lancet, Sep. 3, 1983, pp. 532-534.
Svedman, P., Irrigation Treatment in Split-Thickness Skin Grafting of Intractable Leg Ulcers, Scand J. Plast. Reconst. Surg., 1985, 19, pp. 211-213.
Swift, et al, Quorum Sensing in Aeromonas hydrophila and Aeromonas salmoncida: Identification of LuxRI Homologs AhyRI and AsaRI and Their Cognate N-Acylhomoserine Lactone Signal Molecules, J. Bacteriol., 1997, 179(17):5271-5281.
Usupov, Y. N., et al., "Active Wound Drainage", The Kremlin Papers: Perspectives in Wound Care, Russian Journal: Vestnik Khirurgii, BlueSky Publishing, La Costa, California (2004), 8-10.
Venturi, Mark L., "Mechanisms and Clinical Applications of the Vacuum-Assisted Closure (VAC) Device", Am J Clin Dermatol (2005) 693, 185-194; Review Article (2005), 185-194.
Webb, New Techniques in Wound Management: Vacuum-Assisted Wound Closure, Journal of the American Academy of Orthopaedic Surgeons, v. 10, No. 5, pp. 303-311, Sep. 2002.
Webster's Revised Unabridged Dictionary, published 1913 by C. & G. Merriam Co., definition of Flapper Valve, downloaded from Free Online Dictionary.
Westaby, S., et al., "A Wound Irrigation Device", The Lancet, Sep. 2, 1978, pp. 503-504.
U.S. Appl. No. 14/949,624, filed Nov. 23, 2015, Weston.
U.S. Appl. No. 14/992,818, filed Jan. 11, 2016, Weston.
U.S. Appl. No. 12/260,962, filed Oct. 29, 2009, Weston.
"General Characteristics of Wound Healing and Russian Classificaiton of Wound Healing Process."
3M Health Care, Controlling the Risk of Surgical Site Infections after Cardiovascular Procedures: The Importance of Providing a Sterile Surface, Brochure, St. Paul, MN and London, Ontario, Canada, 1997, 8 pages.
A Sensational Medical discovery, Brit. Journ. Nurs., Jul. 15, 1911, 42.
Agarwala, S., et al., Use of Mini-Vacuum Drains in Small Surgical Wounds, Plastic and Reconstructive Surgery, Apr. 1998, 101(5), 1421-1422 (Correspondence).
Agrama, H.M., Functional Longevity of Intraperiotoneal Drains, Amer. Journ. of Surg., Sep. 1976, 132, 418-421.
Alexander, J. Wesley, "Prevention of Wound Infections," The American Journal of Surgery, Jul. 1976, pp. 59-63, vol. 132, USA.
Alper, J.C., et al., An Effective Dressing for a Large, Draining Abdominal wound, RN, Dec. 24-25, 1988
Alper, J.C., et al., Moist Wound Healing under a Vapor Permeable Membrane, Journ. of Amer. Acad. of Derm., Mar. 1983, 8(3), 347-353.

Alper, Joseph, C., "Recent Advances in Moist Wound Healing," Southern Medical Journal, Nov. 1986, pp. 1398-1404, vol. 79, No. 11 USA.
Arnljots et al., "Irrigation Treatment in Split-Thickness Skin Grafting of Intractable Leg Ulcers," Scandinavian Journal of Plastic and Reconstructive Surgery, 1985, vol. 19, pp. 211-213.
Article Excerpt, Lancet, Jun. 14, 1952, 1175-1176.
Ashrafov, A.A. and K.G. Ibishov, An Experimental and Clinical Validation for the Use of a Collagen Sponge for Treating the Suppurative-Inflammatory Complications of Wound Healing in Emergency Abdominal Surgery, PubMed, Abs. Downloaded from Internet, Apr. 24, 2006, 1 page.
Assessing the Patient with a Fistula or Draining Wounds, Nursing, Jun. 1980, 49-51.
Aubrey, D.A., et al., Treatment of the Perineal Wound after Proctectomy by Intermittent Irrigation, Arch. Surg., Oct. 1984, 119, 1141-1144.
Avocat, C. et al., Nouvelle Presentation de Materiel Pour Drainage de Redon et Jost, La Nouvelle Press Medicale, Jun. 26, 1976, 5(6), 1644-1645 (in French).
Ayoub, M.H. and G. C. Bennet, A Study of Cutaneous and Intracompartmental Limb Pressures Associated with the Combined Use of Tourniquets and Plaster Casts, Abs., Proc. and Reports of Univ., Colleges, Councils, Assoc., and Societies, 68-B:3, May 1986, 497.
Bagautdinov, "Variant of External Vacuum Aspiration in the Treatment of Purulent Diseases of Soft Tissues," Current Problems in Modern Clinical Surgery, 1986, 4 pages.
Baldwin, J.F., Ed., The Columbus Medical Journal, Columbus , Ohio, 1887, V., 561.
Barbul, A., et al., Eds., Clinical and Experimental Approaches to Dermal and Epidermal Repair, Normal and Chronic Wounds, Progress in Clin. and Biol. Res., vol. 365, Proc. of the 3rd Intnl. Symp. on Tissue Repair, Miami, FL, Jan. 10-14, 1990, Abs.
Bar-El, Y. et al., Potentially dangerous Negative Intrapleural pressures Generated by Ordinary Pleural Drainage Systems, Chest, Feb. 2001, 119(2), 511-514.
Barker, D.E., et al., Vacuum Pack Technique of Temporary Abdominal Closure: A 7-Year Experience with 112 Patients, Journ. of Trauma: Injury and Critical Care, Feb. 2000, 4892), 201-207.
Bascom, J., Pilonidal Sinus, Current Therapy in Colon and Rectal Surgery, 1990, 1-8.
Benjamin, P.J., Faeculent Peritonitis: A Complication of Vacuum Drainage, Br. J. Surg., 1980, 67, 453-454.
Berman and Fabiano, Closed Suction Drainage, Orthopedics, Mar. 1990, 13(3), 310-314.
Berman, A. T., et al., Comparison Between Intermittent (Spring-Loaded) and Continuous Closed Suction Drainage of Orthopedic Wounds: A Controlled Clinical Trial, Orthopedics, Mar. 1990, 13(3), 9 pgs.
Besst, J.A., Wound Healing—Intraoperative Factors, Nursing Clinics of North America, Dec. 1979, 14(4), 701-712.
Betancourt, Sergio, "A Method of Collecting the Effluent from Complicated Fistual of the Small Intestine," Dept. of Surgery, Allegheny General Hospital, Pittsburgh, p. 375, USA.
Biblehimer, Helen L., "Dealing With a Wound that Drains 1.5 Liters a Day," RN, Aug. 1986, pp. 21-23, USA.
Bier, A., Hyperemia as a Therapeutic Agent, Ed. Dr. Gustavus M. Blech, A. Robertson & Co., Chicago 1905, (the entire reference has been submitted, but pp. 74-85 may be the most relevant).
Birdsell, D.C., et al., The Theoretically Ideal Donor Site Dressing; Annals of Plastic Surgery, vol. 2, Jun. 1979; Gadgetry, Div. of Plastic Surgery, Foothills, Hospital, Calgary, Canada, 535-537.
Bischoff, et al., Vacuum-Sealing Fixation of Mesh Grafts, Euro. Journ. Plast. Surg., Jul. 2003, 26(4), 189-190, Abs. Downloaded from internet Apr. 6, 2006.
Bonnema, J., et al., A Prospective Randomized Trial of High Versus Low Vacuum Drainage after Axillary Dissection for Breast Cancer, Amer. Journ. Surg., Feb. 1997, 173, 76-79.
Boretos, John W., "Cellular Polymers for Medical Use: The Vital Role of Porosity and Permeability," Cellular Polymers, 1984, vol. 3, pp. 345-358.

(56) References Cited

OTHER PUBLICATIONS

Britton, B.J., et al., A Comparison Between Disposable and Non-Disposable Suction Drainage Units: A Report of a Controlled Trial, *Br. J. Surg.* 1979, 66, 279-280.
Broader, J.H., et al., Management of the Pelvic Space after Proctectomy, *Br. J. Surg.*, 1974, 62, 94-97.
Brubacher, Lynda L., "To Heal a Draining Wound", RN, Mar. 1982, pp. 30-35, USA.
Brummelkamp, W.H., et al, "High-vacuum drainage and primary perineal wound closure in abdominoperineal excision of the rectum", The Netherlands Journal of Surgery, 1991 pp. 236-238, Netherlands.
Bruno, P., The Nature of Wound Healing: Implications for Nursing Practice, *Nursing Clinics of North American*, Dec. 1979, 14(4), 667-682.
Bucalo et al. "Inhibition of Cell Proliferation by Chronic Wound Fluid." Wound Repair and Regeneration. Miami, 1993. pp. 181-186.
Burdette-Taylor, S.R., Use of the Versatile One (V1) for Closed Suction Drainage to Stimulate Closure in Chronic Wounds in Home Care, Case Study Presentation, 2003, 2 pgs.
Bush, G.K., What is a Counter Irritant? Name Any That You Know and the Method of their Application, *Brit. Journ. Nurs.*, Oct. 1927, 232.
Calhoun, P. and K. Kenney, Pouching Management of Patients with Open abdomen, Eviscerations and Bowel Fistulas, *Case Studies, Univ. of Miami/Jackson Memorial Medical Center*, 1 page.
Candiani, P., et al., Repair of a Recurrent Urethrovaginal Fistula with an Island Bulbocavernous Musculocutaneous Flap, *Plastic and Reconstructive Surgery*, Dec. 1993, 1393-1394.
Carroll, P.L., The Principles of Vacuum and its Use in the Hospital Environment, 2nd Ed., 1986, 30p.
Chardak et al., "Experimental Studies on Synthetic Substitutes for Skin and Their Use in the Treatment of Burns," Annals of Surgery, 1962, vol. 155, No. 1, pp. 127-139.
Chariker, M.E., et al, "Effective Management of Incisional and Cutaneous Fistulae with Closed Suction Wound Drainage," Contemporary Surgery. Jun. 1989, pp. 59-63, vol. 34 USA.
Chart: Influence of Wound Closure on Healing of Perineal Wound after Abdominoperineal Resection or Total Proctocolectomy, excerpt faxed Jan. 23, 2006, 1 page.
Chua Patel, C.T., et al., Vacuum-Assisted Closure, *AJN*, Dec. 2000, 100(12), 45-49.
Cobb, J.P., Why Use Drains?, *Br. J. Bone Joint Surg.*, Nov. 1990, 72-B(6), 993-995.
Cooper, D.M., Optimizing Wound Healing, *Nursing Clinics of North America*, Mar. 1990, 25(1), 163-179.
Cooper, D.M., Postsurgical Nursing Intervention as an Adjunct to Wound Healing, *Nursing Clinics of North America*, Dec. 1979, 14(4), 713-726.
Cooper, S.M. and E. Young, Topical Negative Pressure, *Commentary, International Journal of Dermatology 2000*, 39, 892-898.
Costunchenok, B.M., et al., Effect of Vacuum on Surgical Purulent Wounds, *Vestnik Chirurgia 1986*, Sep. 18-20 (in Russian with English translation).
Cotton, P.B., et al., Early Endoscopy of Oesophagus, Stomach, and Duodenal Bulb in patients with Haematemesis and Melaena, *Br. Med. Journ.*, Jun. 2, 1973, 505-509.
Crisp, W.J. and A. Gunn, Granuflex Dressings for Closed Surgical Wounds Combined with Suction Drainage, *Annals of the Royal College of Surgeons of England*, 1990, 72, p. 76.
Cucuroos, Y.C., Vacuum Drainage of Post Operative Wounds, *Kiev Army Hospital, Dept. of Hospital Surgery, Kiev medical University*, 64-65 (in Russian with English translation).
Curtin, L.L., Wound Management: care and Cost—an Overview, *Nursing Management*, Feb. 1984, 15(_), 22-25.
Davydov et al. "Pathogenic Mechanism of the Effect of Vacuum Therapy on the Course of the Wound Process" Dec. 1986.

Davydov, Y.A., et al. Justifying the Usage of Force Early Secondary Sutures in treatment of Purulent Wounds by the Vacuum Therapy, Vestnik Chirugia 1990, March Edition, 126-129 (in Russian with English translation).
Davydov, Y.A., et al., Concept of Clinico-Biological Management of Wound Process in Treatment of Purulent Wounds with the Help of Vacuum Therapy, Vestnik Chirurgia 1991, February Edition, 132-135 (in Russian with English Translation).
Davydov, Y.A., et al., The Bacteriological & Cytological Assessment of Vacuum Therapy of Purulent Wounds, Vestnik Chirurgia 1988, October Edition 48-52 (in Russian with English translation). 1987.
Davydov, Y.A., et al., Vacuum Therapy in The Treatment of Purulent Lactational Mastitis, Vestnik Chirurgia, Grexova 1986, September Edition, 66-70 (in Russian with English translation).
Davis, J.C. and T.K. Hunt, Eds., Problem Wounds: The Role of Oxygen, Chap. 1, Infection and Oxygen, 1988,1-15.
Dilmaghani et al., "A Method for Closed Irrigation and Suction Therapy in Deep Wound Infections," Journal of Bone and Joint Surgery, 1969, vol. 51-A, No. 2, pp. 323-342.
Doillon, C.J., et al., Collagen-Based Wound Dressings: Control of the Pore Structure and Morphology, Journal of Biomedical Materials Research, Sep. 13, 2004, 20(8), 1219-1228. Abs. Downloaded from Internet http://www3.interscience.wiley.com, Apr. 28, 2006.
Domkowski, P.W., et al., Evaluation of Vacuum-Assisted Closure in the Treatment of Poststernotomy Mediastinitis, *Journ. of Thorac. and Cardiovascular Surg.*, Aug. 2003, 126(2), 386-390.
Doss, Mirko, et al., Vacuum-Assisted Suction Drainage Versus Conventional Treatment in the Management of Poststernotomy Osteomyelitis, *Euro. Journ. Cardio-Thoracic. Surg.* 22 ((2002) 934-938.
Draper, J., Make the Dressing Fit the Wound, *Nursing Times*, Oct. 9, 1985, 32-35.
Dunbar, J.M., State What You Have Learned Recently on the Up-to-Date Care of Wounds, *Brit. Journ. Nurs.*, Dec. 1941, 200.
Dunlop, M.G, et al. Vacuum Drainage of Groin Wounds after Vascular Surgery: A Controled Trial, Br. J. Surg., May 1990, 77, 562-563.
Eaglstein, W.H., et al., Wound Dressings: Current and Future, *Clin. and Exper. Approaches to Dermal and Epidermal Repair: Normal and Chronic Wounds*, 1991, 257-265.
ECRI, Target Report, Negative Pressure Wound Therapy for Chronic Wounds, Jan. 24, 2006, 1-7, Downloaded from internet, http://www.target.ecri.org/summary/detail.aspx?dox_id=1155.
Eisenbud, D.E., Modern Wound Management, *Anadem Publishing*, Chap. 16, 109-116, 2000.
Ellingwood, F., Ellingwood's Therapeutist, Jun. 14, 1908, 2(6), 32-33.
Elwood, E.T., and D.G. Bolitho, Negative-Pressure Dressings in the Treatment of Hidradenitis Suppurative, *Annals of Plastic Surgery*, Jan. 2001, 46(1), 49-51.
Engdahl, O. and J. Boe, Quantification of Aspirated Air Volume reduces Treatment Time in Pneumothorax, *Eur. Respir, J.*, 1990, 3, 649-652.
Engdahl, O., et al., Treatment of Pneumothorax: Application of a Technique which Quantifies Air Flow Through the Chest Drain, *Adv. in Therapy*, May/Jun. 1988, 5(3), 47-54.
Erichsen, J.E., Science and Art of Surgery, London: *Longmans, Green, and Co., 1895*, vol. 1, 258-259, and p. 289.
Fabian, T.S., The Evaluation of Subatmospheric Pressure and Hyperbaric Oxygen in Ischemic Full-Thickness Wound Healing, *Ischemic Full-Thickness Wound Healing*, Dec. 2000, 66(12), 1136-1143.
Fay, M.F., Drainage Systems: Their Role in Wound Healing, *AORN Journal*, Sep. 1987, 46(3), 442-455.
Fellin, R., Managing Decubitus Ulcers, *Nursing Management*, Feb. 1984, 29-30.
Fingerhut, A., et al., Passive vs. Closed Suction drainage after Perineal Wound Closure Following Abdominoperineal Rectal Excision for Carcinoma, *Dis Colon Rectum*, Sep. 1995, 926-932.
Finley, John M.,"Practical Wound Management," pp. 45, 127, 143, 149, 207, 1981.

(56) References Cited

OTHER PUBLICATIONS

Firlit, C.F. and J.R. Canning, Surgical Wound Drainage: A Simple Device for Collection, *Journ. of Urology*, Aug. 1972, 108, p. 327.
Fisher, Jack, and R. W. Bert, Jr., A Technique for Skin Grafting Around Abdominal Wall Fistulas, *Annals of Plastic Surgery*, 11:6, Dec. 1983, 563-564.
Flanagan, et al., Optional Sump: Novel Use of Triple Lumen Closed Drainage System, *Anz. J. Surg.*, Nov. 2002, 72(11), 806-807, Abs. Downloaded from internet Nov. 30, 2003.
Fleck, C.A., When Negative is Positive: A Review of Negative Pressure Wound therapy, *Wound Care*, Mar./Apr. 20-25, 2004.
Fleischmann, "Vacuum sealing: indication, technique, and results," *European Journal of Orthopaedic Surgery & Traumatology*, vol. 5(1), 1995, pp. 37-40.
Fleischmann, W. Wund Forum Spezial, "Vakuumversiegelung zur Behandlung von Problemwunden" (with English translation: Vacuum Sealing for Treatment of Problematical Wounds), *IHW '94*, 6 pages.
Flynn, M.E. and D.T. Rovee, Wound Healing Mechanisms, *Amer. Journ. of Nursing*, Oct. 1982, 1544-1556.
Fox, J.W. and G.T. Golden, The Use of Drains in Subcutaneous Surgical Procedures, *Amer. Journ. of Surg*, Nov. 1976, 132, 673-674.
Garcia-Rinaldi, R., et al., Improving the Efficiency of Wound Drainage Catheters, *Amer. Journ. of Surg.*, Sep. 1975, 130, 372-373.
Geiger Jones, E., et al., Management of an Iliostomy and Mucous Fistula Located in a Dehisced Wound in a Patient with Morbid Obesity, *J. WOCN*, Nov. 2003, 30(6), 351-356.
Gill, P., What is a Counter-Irritant? Name Three and the Method of Applying them, *Brit. Journ. Nurs.*, Jun. 1934, 142.
Goddard, L., Inflammation: Its Cause and Treatment, *Brit. Journ. Nurs.*, Jan. 1944, 2.
GOMCO Suction Equipment & Accessories Guide, Catalog, Apr. 2006, 20 pages.
Gouttefangeas, C. et al., Functional T Lymphocytes Infiltrate Implanted Polyvinyl Alcohol Foams During Surgical Wound Closure Therapy, *Clin. Exp. Immunol.* 2001, 124, 398-405.
Grabowski, S., Leczenie ran z zastosowaniem posicśnienia (wg Redona I Josta), *Il Klinik Xhieuefxnej AM w Warszawie; klerownik: Prof. Dr. Z. Lapinski*, No. 1, 19-21 (in Polish).
Greene, M. A., et al. Laparotomy Wound Closure with Absorable Polyclycolic Acid Mesh, Surgery, Gynecology and Obsterics Mar. 1993; vol. 176, pp. 213-218.
Grishdevich, V. and N. Ostrovsky, Postburn Facial Resurfacing with a Split Ascending Neck Flap, *Plastic and Reconstructive Surgery*, Dec. 1993, 1384-1391.
Grobmyer, et al., High-Pressure Gradients Generated by Closed-Suction Surgical Drainage Systems, *Surg. Infect. (Larchmt), Autumn 2002*, 3(3), 245-249, Abs., Downloaded Nov. 30, 2003.
Grover, R. and R. Sanders, Recent Advances: Plastic Surgery, Clinical Review, *BMJ*, Aug. 8, 1998, 317, 397-400.
Gupta, S., Ed., Guidelines for Managing pressure Ulcers with Negative Pressure Wound Therapy, *Advances in Skin & Wound Care Suppl.*, Nov./Dec. 2004, 17(2), 1-16.
Gupta, S., Guidelines for Managing: Pressure Ulcers with Negative Pressure Wound Therapy, Downloaded from internet http://proquest.umi.com on Feb. 3, 2006. 19 pages.
Gwan-Nulla, D.N. and R.S. Casal, Toxic Shock Syndrome Associated with the Use of the Vacuum-Assisted Closure Device, Ann. Plast. Surg., Nov. 2001, 47(5), 552-554.
Hallstrom, B.R. and J.F. Steele, Postoperative Course after Total Hip Arthroplasty: Wound Drainage versus No Drainage, Orthopaedic Review, Jul. 1992, 847-851.
Hanbok för Hälso-Och Sjukvårdsarbete Lokal Anvisning för Landstinget Sörmland, Jan. 2001, 7 pgs, (in Swedish), Downloaded from Internet http://www.landstinget.sormland.se, Aug. 14, 2001, 7 pages.
Harkiss, K., Cheaper in the Long Run, *Community Outlook*, Aug. 19-22, 1985.

Harle, A. Z. Orthop., 127: 513-517 (1989), "Schwachstellen herkommlicher Drainagen."
Hartz, R.S., et al., Healing of the Perineal Wound, *Arch. Surg.*, Apr. 1980, 115, 471-474.
Harvard Pilgrim Health Care, Technology Assessment Policy, TA 6.29 Negative Pressure Wound therapy for Wound Healing, Dec. 1-6, 2004.
Hay, J., et al., Management of the Pelvic Space With or Without Omentoplasty after Abdominoperineal Resection for Carcinoma of the Rectum: a Prospective Multicenter Study, *Eur. J. Surg*, 1997, Abs.
Higgins, S., The Effectiveness of Vacuum Assisted Closure (VAC) in Wound Healing, *Centre for Clinical Effectiveness, Monash Medical Centre, Clayton VIC Australia*, Dec. 1-16, 2003.
Hilsabeck, J.R., The Presacral Space as a Collector of Fluid Accumulations Following Rectal Anastomosis: Tolerance of Rectal Anastomosis to Closed Suction Pelvic Drainage, Amer. Soc. of Colon and Rectal Surgeons, vol. 25, No. 7, Oct. 1982.
Hilton, P., Wound Drainage: A Survey of Practices among Gynaecologists in the British Isles, *Br. Journ. of Obstetrics and Gynaecology*, Oct. 1988, 95, 1063-1069.
Hollis, H.W. and M.R. Troy, A Practical Approach to Wound care in patients with Complex Enterocutaneous Fistulas, *Surg., Gyn. & Obs.*, Aug. 1985, 161, 179-181.
Hugh, T.B., Abdominal Wound Drainage, *Med. Journ. of Australia*, May 4, 1987, 146, p. 505 (Correspondence).
Hulten, L., et al., Primary Closure of Perineal Wound after Proctocolectomy or Rectal Excision, *Acta Chir. Scand.*, 1971, 137, 467-469.
Hunt, T.K. and J.E. Dunphy, Eds., Fundamentals of Wound Management, *Appleton-Century-Crofts/New York*, 416-447, 1979.
Ilizarov, G.A., The Tension-Stress Effect on the Genesis and Growth of Tissues: Part II., *Clinical Orthopaedics and Related Research*, Feb. 1989, 239, 263-283.
International Standard ISO 10079-1, First Edition, May 15, 1991, 2 pages.
Izmailov, S.G., et al., Device for Treatment of wounds and Abdominal Cavity, Contents, Surg. Nov. 8, 1997, Downloaded from internet http://www.mediasphera.ru/surgery/97/8/e8-97ref.htm.
Izmailov, S.G., The Treatment of Eventrations with a Special Apparatus, Abstracts, Surg. Nov. 1, 1997, Downloaded from internet, http://www.mediasphera.ru/surgery/97/1/e1-97ref.htm.
Jeter, K., Closed Suction Wound Drainage System, *J. WOCN*, Mar./Apr. 2004, 51 (correspondence).
Jeter, Katherine F. ET, Managing Draining Wounds and Fistulae: New and Established Methods, Chronic Wound Care, Chapter 27, pp. 240-246, 1990.
Johnson, F.E., An Improved Technique for Skin Graft Placement using a Suction Drain, *Surgery, Gynecology & Obstetrics*, Dec. 1984, 159(6), 584-585.
Kazan Medical Institute Doctors, A Gadget to Bring the Wound Edges Close, 78-79 (in Russian with English translation). Aug. 20, 1985.
KCI, Inc., If It's Not V.A.C. Therapy, It's Not Negative Pressure Wound Therapy, *KCI Brochure*, Jan. 1-5, 2005.
KCI, Inc., Introducing the V.A.C. GranuFoam Silver Dressing, *Flyer*, 2 pages.
KCI, Inc., The V.A.C. System, 2000-2001, Brochure, 2 pgs.
KCI, Inc., Vacuum Assisted Closure (VAC) from Wound Healing, *Evidence Note 5, NHS Quality Improvement Scotland*, Nov. 2003, 1 page.
Keen, W.W., Ed., Surgery, Its Principles and Practice, 1919, W. B. Saunders Company, p. 56, excerpt, 1919.
Keith, C.F., Wound management Following Head and Neck Surgery, *Nursing Clinics of North America*, Dec. 1979, 14(4) 761-779.
Kennard, H.W., Bier's Hyperaemia, *Brit. Journ. Nurs.*, Mar. 20, 1909, 223.
Khil'kin, A.M., Use of a Collagen Hemostatic Sponge for the Experimental Closing of the Surface of a Liver Wound (article in Russian), Citation Downloaded from internet http://www.ncbi.nlm.nih.gov Apr. 24, 2006.

(56) References Cited

OTHER PUBLICATIONS

Kiemele, L.J., et al., Catheter-Based Negative Pressure Wound Therapy: A New Paradigm of Care, *Nursing Home Wound Care consultative Service*, Mayo Clinic, Rochester, MN. 2 pages.

Kim, S.H., et al., Wangensteen Suction Drainage, apparatus in Neurosurgical Practice, *Dept. of Neurosurgery, Yonsei University of College of Medicine*, Seoul, Korea, 1975, 159-160, Abs. (in Korean and Abstract in English).

Kloth, L.C. and J.M. McCulloch, Wound Healing Alternatives in Management, 3rd Ed., Chap. 10, 339-352, 2002.

Knight, Marie Ray, "A Second Skin for Patients with Large Draining Wounds," Nursing, Jan. 1976, p. 37, USA.

Kohlman, Phyllis A., et al, "Pouching Procedure to Collect Drainage From Around a Biliary Drainage Catheter," Ostomy/Wound Management, Nov./Dec. 1991, pp. 47-50, vol. 37.

Kordasiewicz, L.M., Abdominal Wound with a Fistula and Large Amount of Drainage Status after Incarcerate Hernia Repair, *J. WOCN*, May/Jun. 2004, 31(3), 150-153.

Kremlin Papers, A Collection of Published Studies Complementing the Research and Innovation of Wound Care, from *Vestnik Khirurgii, BlueSky Publishing, A Div. of BlueSky Medical Group Inc.*, 2004. 17 pages.

Landes, R.R. and I. Melnick, An Improved Suction Device for Draining Wounds, *Arch. Surg.*, May 1972, 104, p. 707.

Landis, E.M. and J.H. Gibbon, Jr., The Effects of Alternate Suction and Pressure on Blood Flow to the Lower Extremities, Alternate Suction and Pressure, J Clin Invest. Sep. 1933, 12(5): 925-961.

Larichev, A.B., Vacuum Therapy of Wounds and Wound Infection, *1st. Ed., BlueSky Publishing*, 2005.237 pgs.

Lee, J.H. and H.J. Yang, Application of Medifoam B® & Negative Pressure Therapy for the Auxiliary Treatment of Pressure Sore, *Dept. Plastic and Reconstructive Surg., College of Medicine, Eulji Univ.*, Daejeon, Korea, Abs. Sep. 31, 2004, 1 page.

Linden van der, Willem, Randomized Trial of Drainage After Cholecystectomy, Modern Operative Techniques, Voluje 141, Feb. 1981, pp. 289-294.

Lockwood, C.B., Aseptic Surgery, Drainage, *Brit. Journ. Nurs.*, Mar. 26, 1904, 245.

Luchette, F.A., When Should the General Surgeon Leave the Abdomen Open?, Division of Trauma, Surgical Critical Care and Burns, Loyola University Medical Center, Maywood, Illinois., 37 pages (date N/A).

Lumley, J.S.P., et al., The Physical and bacteriological Properties of Disposable and Non-Disposable Suction Drainage Units in the Laboratory, *Br. J. Surg.*, 1974, 61, 832-837.

Lundvall, J. and T. Lanne, Transmission of Externally applied Negative pressure to the Underlying Tissue: A Study on the Upper Arm of Man, *Acta Physiol. Scand.* 1989, 136, 403-409.

Magee, C., et al., Potentiation of Wound Infection by Surgical Drains, *Amer. Journ. of Surg.*, May 1976, 131, 547-549.

Mayo, C.W., The One-Stage Combined Abdominoperineal Resection for Carcinoma of the Rectum, RectoSigmoid and Sigmoid, *Surgical Clinics of North America*, Aug. 1939, Mayo Clinic Number, 1011-1012.

McFarlane, R. M., "The Use of Continuous Suction Under Skin Flaps", F.R.C.S.(c), vol. 1, pp. 77-86 (1958).

McGuire, S., Drainage after Abdominal Section, *Br. Journ. of Nurs.*, Dec. 15, 1903, 447-449.

McLaughlan, James, Sterile Microenvironment for Postoperative Wound Care, The Lancet, pp. 503-504, Sep. 2, 1978.

Medela, Inc., Pleupump MK II, Aug. 14, 2001, Brochure (in German). 12 pages.

Mendez-Eastman, S., Guidelines for Using Negative Pressure Wound Therapy, *Advances in Skin & Wound Care*, 14(6), Nov./Dec. 2001, 314-325.

Mendez-Eastman, S., When Wounds Won't Heal, *RN*, Jan. 2-7, 1998.

Meyer and Schmieden, Bier's Hyperemic Treatment, Fig. 69-70, 557.

Meyer and Schmieden, Bier's Hyperemic Treatment, *Published 1908 W. B. Saunders Company*, 44-65.

Meyer, W. & Schmieden, V., *Bier's Hyperemic Treatment, W B. Saunders Company* 1908, (the entire reference has been submitted, but pp. 44-65 may be the most relevant).

Miles, W. Ernest, "Technique of the Radical Operation for Cancer of the Rectum", The British Journal of Surgery,pp. 292-304, United Kingdom 1914-1915.

Miles, W.E., A Method of Performing Abdominoperineal Excision for Carcinoma of the Rectum and of the Terminal Portion of the Pelvic Colon, *The Lancet*, Dec. 19, 1908, 1812-1813.

Miller, M.S. and C. McDaniel, Treating a Pilonidal Cystectomy Abscess Wound with the BlueSky Medical Versatile 1™ Negative Pressure Wound Therapy, *The Wound Healing Center, Terre Haute, Indiana, Case Study 2004-2006*, 1 page.

Miller, M.S., Negative Pressure Wound Therapy: "A Rose by Any Other Name," *Ostomy/Wound Management*, Mar. 2005, 51(3), 44-49.

Milsom, I. and A. Gustafsson, An Evaluation of a Post-Operative Vacuum Drainage System, *Curr. Med. Res. Opin.* (1979), 6, 160-164.

Moloney, G. E., "Apposition and Drainage of Large Skin Flaps by Suction", ANZ Jourjal of Surgery vol. 26, Issue 3, Feb. 1957, pp. 173-179.

Morykwas, M.J., et al., Effects of Varying Levels of Subatmospheric Pressure on the Rate of Granulation Tissue Formation in Experimental Wounds in Swine, *Abs., Ann. Plast. Surg. 2001*, 47: 547.

Moserova, J. and E. Houskova, The Healing and Treatment of Skin Defects, 1989, 116-143.

Moss, W., What is Cellulitis? Describe Some Forms of Treatment You Would Expect to be Used for Cellulitis of the Arm, *Brit. Journ. Nurs.*, Nov. 1935, 282.

Mulder, G.D., Ed., et al., Clinicians' Pocket Guide to Chronic Wound Repair, *Wound Healing Publications*, Spartanburg, SC, 1991, 54-55.

Mullner, T., et al., The Use of Negative Pressue to Promote the Healing of Tissue Defects: A Clinical Trial Using the Vacuum Sealing Technique, *Br. J. Plast. Surg.*, Apr. 1997, 51(1), 79, Abs.

Musashaikhov, K.T., et al., The Course of Wound Healing under the Influence of Polyphepan in patients with Diabetes Mellitus, Abstracts, Surg. No. 5, 1997, Downloaded from internet, http://www.mediasphera.ru/surgery/97/5/e5-97ref.htm, 1 page.

Nakayama, Y., et al., "A New Method for the Dressing of Free Skin Grafts", Plastic and Reconstructive Surgery, Dec. 1990 pp. 1216-1219, UK.

Nakayama, Yoshio, et al., A New Method for Dressing of Free Skin Grafts, New Method for Free Skin Grafting, vol. 86, No. 6 Jun. 12, 1990.

Nasser, A.N., The Use of the Mini-Flap Wound Suction Drain in maxillofacial Surgery, *Annals of the Royal College of Surgeons of England*, 1986, 68, 151-153.

Navsaria, P.H., et al., Temporary Closure of Open Abdominal Wounds by the Modified Sandwich-Vacuum Pack Technique, *Br. Journ. Surg., 2003*, 90, 718-722.

Nghiem, D.D., A Technique of Catheter insertion for Uncomplicated Peritoneal Dialysis, *Surgery, Gynecology & Obstetrics*, Dec. 1983, 157, 575-576.

Nicholas, J.M., Options for Management of the Open Abdomen, Presentation from Emory University School of Medicine, 66 pgs. Invited Speaker American College of Surgeons 32nd Annual Spring Meeting, General Session 12—Presentation and Panel Discussion on The Open Abdomen in General Surgery—How Do You Close the Abdomen When You Can't—Bostom Marriott Copley Place Hotel, Boston, MA Apr. 26, 2004.

Nightingale, K., Making Sense of wound Drainage, *Nursing time* Jul. 5, 1989, 85(27), 40-42.

Noblett, E.A., What is an Empyema? What Operations are Undertaken for its Relief, and What Have You to Say About the After-Nursing?, Brit. Journ. Nurs., Apr. 29, 1916, 375.

NURSING75, Wound Suction: Better Drainage with Fewer Problems, Nursing, vol. 5, No. 10, Oct. 1975, pp. 52-55.

(56) References Cited

OTHER PUBLICATIONS

O'Byrne, C., Clinical Detection and Management of Postoperative Wound Sepsis, *Nursing Clinics of North American*, Dec. 1979, 14(4), 727-741.

Ohotskii, V.P., et al., Usage of Vacuum Suction During the Primary Surgical Debridement of Open Limb Injuries, *Sovetskaya Medicina*, Jan. 17-20, 1973 (in Russian with English translation).

Ontario Ministry of Health and Long Term Care for the Ontario Health Technology Advisory Committee, "Vacuum Assisted Closure Therapy for Wound Care, Health Technology Literature Review," Dec. 2004, Toronto, Ontario, Canada, pp. 1-57.

Orgill, D. P., et al., Microdeformational Wound Therapy—A New Era in Wound Healing, *Tissue Engin. and Wound Healing Laboratory, Brigham and Women's Hospital, Business Briefing: Global Surgery—Future Direction 2005*, 22.

Orgill, D., et al., Current Concepts and Approaches to Wound Healing, *Critical Care Medicine*, Sep. 1988, 16(9), 899-908.

Orgill, D.P., et al., Guidelines for Treatment of Complex Chest Wounds with Negative Pressure Wound Therapy, *Wounds, A Compendium of Clinical Research and Practice, Suppl. B*, Dec. 2004, 1-23.

Oschsner, A.J., Surgical Diagnosis and Treatment, 1921, 11, 266-269.

Parker, M.J. and C. Roberts, Closed suction Surgical Wound Drainage after Orthopaedic Surgery, *Cochran Database of Systematic Review 2005*, 3, 3 pages.

Parulkar, B.G., et al., Dextranomer Dressing in the Treatment of Infected Wounds and Cutaneous Ulcers, *J. Postgrad. Med.*, 1985, 31(1), 28-33.

Penman, M., What Are the Signs and Symptoms of Gallstones? What Instruments Would You have Ready for the Operation? How Would You Nurse a Case After Operation?, *Brit. Journ. Nurs.*, Aug. 9, 1919, 88.

Pham, C., et al., Vacuum-Assisted Closure for the Management of Wounds: An Accelerated Systematic Review, *Asernip-Accelerated Review of Vacuum Assisted Wound Closure, Report No. 27*, Dec. 2003, 1-52.

Precision Medical, Power VAC+ Intermittent Aspirator, http://precisionmedical.com Downloaded from internet Apr. 10, 2006, 2 pages.

Putney F. Johnson, "The Use of Continuous Negative Pressure after Laryngectomy and Radical Neck Dissection", *Surgery, Gynecology & Obstetrics*, Aug. 1956, pp. 244-246, USA.

Raffl, Arthur B., "Use of Negative Pressure Under Skin Flaps After Radical Mastectomy,"Dept. of Surgery, State Univ. of N.Y., College of Medicine, Syracuse, NY, Submitted for publication Apr. 1953, p. 1048, USA.

Ramirez, O.M., et al., Optimal Wound Healing under Op-Site Dressing, *Ideas and Innovations*, 73(3), pp. 474-475.

Rammensee, H.G., Untersuchung der Lymphozytenin filtrate in Implantierte PVA-Schwämme nach der Therapie infizierter Wunden mit Vakuumversiegelung, Aus dem Interfakulatären Institut für Zellbiologie der Universitat Tubingen Abeilung Immunologie Abteilungsleter, 2004, 119 pgs.

Ranson, John H. M.D., Safer Intraperitoneal Sump Drainage, *Surgery Gynnecology and Obstetrics*, pp. 841-42, 1973 vol. 137.

Redon, H. and J. Troques, La Fermeture Sous Depression des Plaies Etendues, *Academe de Chirurgie*, Mar. 1954, 304-306. (in French).

Redon, H., Closure of Large Wounds under a Partial Vacuum, Paris, *Notes on Practical Medicine, published under L. Rouques*, 1-3.

Reedy, J., The Science Behind Wound Healing, *UW Health Sciences/UW Medicine News and Community Relations*, Winter/Spring 2005, 4 pages.

Reference Handbook of the Medical Sciences, *Hyperaemia*, 553.

Reid, Daniel P., Information on Cupping or Using Suction Cups on Wounds and for Healing Purposes, *Chinese Herbal Medicine*, 2 pages.

Reimann, D., et al., Successful Treatment Due to Vacuum Seal Technique of a Severe Scedosporium Apiospermum Skin Infection in a Renal Transplant Recipient, *Nephrol. Dial. Transplant*, 2004, 19 (1), 245-248.

Richter, Treatment of Inflammatory Conditions of the Skin with Hot Baths, *Brit. Journ. Nurs.*, Aug. 25, 1906, 149.

Roberts, R.H., et al., Randomised Trial of Medinorm LVS and Surgivac Drainage System after Operations for Breast Cancer May 1999, *Amer. Journ. Surg.*, Feb. 1997, 2 pgs.

Robertson, "The Influence upon Wound Contraction of a Negative Interstitial Fluid Pressure Within Granulation Tissue," Journal of Anatomy, 1969, vol. 105, No. 1, pp. 189.

Rodrigo, J.J., et al., The Effect of Varying Degrees of Suction Pressure on Drainage of Hematomas, *Dept. of Orthopaedic Surgery, University of California, David, Sacramento, California*, 9 pages (date N/A).

Rosser, C.J., et al., A New Technique to Manage Perineal Wounds, *Infections in Urology*, Mar./Apr. 2000, 4 pgs.

Royle, G.T. and B.J. Britton, Disposable Drains, *Articles of the Royal College of Surgeons of England*, (1984), vol. 66, 1 page.

Russ and Fleischmann, Vakuumversiegelung, List of References (in English and German), 2000, 4 pgs.

Sagi, A., Burn Hazard from Cupping—An Ancient Universal Medication Still in Practice, *burns*, 1988, 14(4), 323-325.

Sames, C.P., Sealing of Wounds with Vacuum Drainage, *Br. Med. Journ.*, Nov. 5, 1977, p. 1223, Correspondence.

Samson, D., et al., Wound-Healing Technologies: Low-Level Laser and Vacuum-Assisted Closure, *Evidence report/Technology Assessment*, No. 111, Dec. 2004, AHRQ Publication No. 05-E005-2 97 pages.

Sandahl, L., Slides at Geisinger Medical Center, Danville, PA, Apr. 10, 1990, Correspondence, 4 pages.

Schaffer, D.B., Closed Suction Wound Drainage, Nursing97, Nov., Downloaded from internet www.springnet.com, 62-64. 1997.

Schumann, D., Preoperative Measures to Promote Wound Healing, *Nursing Clinics of North America*, Dec. 1979, 14(4), 683-699.

Schwab, Peter M. and Kelly, Keith A., "Primary closure of the Perineal Wound After Proctectomy," Mayo Clinic Proc., Mar. 1974, pp. 176-179, vol. 49, US.

Scott, F., Babies in Bottles, *Advance for Resp. Care Practitioners*, Nov. 23, 1992, 2 pgs.

Senyutovich, R.V., Napkin Preventing Abdominal Contamination in Performance of Colonic Anastomosis, Abstracts, Downloaded from internet, http://www.mediasphera.ru/surgery/97/1/el-97ref.htm— 1997, 1 page.

Shaer, W.D., et al., Inexpensive Vacuum-Assisted Closure Employing a Conventional Disposable Closed-Suction Drainage System, *Plastic and Reconstructive Surgery*, Jan. 2001, 292.

Sheen, A.W., Some Experiences of Shell Wounds in the Present War, (excerpt), *Brit. Journ. Nurs.*, Jan. 16, 1915, 42.

Sheppard, M.D., "Sealed Drainage of Wounds", The Lancet, Jun. 14, 1952, pp. 1174-1176.

Smith, L.A., et al., Vacuum Pack Technique of Temporary Abdominal Closure: A Four-Year Experience, *Amer. Surg.*, Dec. 1997, 63(12), 1102-1108.

Spahn, Slide presented at the WOCN meeting in Ontario, California, Sep. 2001.

Spengler, Michael D., el al, "Performance of Filtered Sump Wound Drainage Tubes", Surgery, Gynecology & Obstetrics, Mar. 1982, pp. 333-336, vol. 54, USA.

Stewart, M. F., et al., Cleaning v Healing, *Community Outlook*, Aug. 22-26, 1985.

Surgidyne, Closed Systems for Management of Wound Drainage, Brochure and Catalog, Downloaded from internet, www.sterion.com, 6 pages (date N/A).

Svedman, P., A Dressing Allowing Continuous Treatment of a Biosurface, *IRCS Med. Science: Biomed. Tech.; Clinic. Med.; Surg. and Transplantation*, 1979, 7, p. 221.

Svedman, P., et al., "A Dressing System Providing Fluid Supply and Suction Drainage Used for Continuous or Intermittent irrigation," Annals of Plastic Surgery, vol. 17, No. 2, Aug. 1986, pp. 125-133.

Swanson, L., Solving Stubborn-Wound problem Could Save Millions, Team Says, *JAMC, 23 FEVR*, 1999: 160(4), p. 556.

(56) References Cited

OTHER PUBLICATIONS

Taylor, Virginia, "Meeting the Challenge of Fistulas & Draining Wounds", Nursing, Jun. 1980, pp. 45-51, USA.
Teder and Svedman et al., "Continuous Wound Irrigation in the Pig," Journal of Investigative Surgery, 1990, vol. 3, pp. 399-407.
Tennant, C.E., "The Use of Hyperemia in the Postoperative Treatment of Lesions of the Extremities and Thorax," Jour. A. M. A., May 8, 1915, pp. 1548-1549.
The British Journal of Nursing, Nov. 4, 1911, 368.
Thomas, Stephen "Wound Management and Dressings" 35-42 (1990).
Tittel, K. and G. Tolksdorff, Forum: VariDyne—Neue Standard in der Postoperative Wunddrainage (New Standards in Postoperative Wound Drainage), *Unfallchirurgie*, 1988 14(2), 104-107 (in German with English Translation).
Tribble, David E. M.D., An Improved Sump Drain-Irrigation Device of Simple Construction, Archives of Surgery New York, pp. 511-513, 1972 vol. 105.
Tuberculous Joints, *Nursing record & Hospital World*, Apr. 28, 1894, 280.
U.S. Appl. No. 11/491,578, filed Jul. 24, 2006, Title: Negative Pressure Protection System.
U.S. Appl. No. 11/654,926, filed Jan. 17, 2007, Title: Container and Cover System.
U.S. Appl. No. 11/784,021, filed Apr. 5, 2007, Title: Instructional Medical Treatment System.
Unknown, "The RN Magazine/University of California Continuing Education Curriculum; Examination on 'To heal a draining wound'", RN, Mar. 1982, p. 36, USA.
Unknown, Medela product information in , English Summary: "Pleupump MK II is the new micro-data controlled thoracic drainage".
Urschel, J.D., et al., The Effect of Mechanical Stress on Soft and Hard Tissue Repair; A Review, *Br. Journ. Plast. Surg.*, 1988, 41, 182-186.
Usypov, Y. N. and M.V. Ephfanov, Active Drainage of wounds, Dept. of Hospital Surgery, Army Medical Academy, Leningrad, *Vestnik Chirurgia 1987*, Apr. Edition, 42-45 (in Russian with English translation).
Valenta, A.L., Using the Vacuum Dressing Alternative for Difficult Wounds, *AIN*, Apr. 1994, 44-45.
Van Heurn, L.W.E. and P.R.G. Brink, Prospective Randomized Trial of High versus Low Vacuum Drainage after Axillary Lymphadenectomy, *Br. Journ. Surg.* 1995, 82, 931-932.
Van Way III, C.W., Prevention of Suction-Induced Gastric mucosal damage in Dogs, *Critical Care Medicine*, Aug. 1987, 15(8), 774-777.
Varley, G.W. and S.A. Milner, Wound Drains in Proximal Femoral Fracture Surgery: A Randomized prospective Trial of 177 Patients, *J. R. Coll. Surg. Edinb.*, Dec. 1995, 40, 416-418.
Vijanto, J. and J. Raekallio, Local Hyperalimentation of Open Wounds, *Br. J. Surg.*, 1976, 63, 427-430.
Wackenfors, A., et al., Effects of Vacuum-Assisted Closure Therapy on Inguinal Wound Edge Microvascular Blood Flow, *Wound Rep. Reg*, 2004, 12, 600-606.
Warren, J.C. and A.P. Gould, Ed., The International Text-Book of Surgery, 1902, 1, 70-79.
Waymack, J. P., et al.: "An evaluation of Aquaphor Gauze dressing in burned children", Burns Include therm Inj. Aug. 1986;12(6):443-8.
Wayne, M.A., Cook Pneumothorax Catheter Set, Wayne Pneumothorax Catheter Set, *Cook Critical Care, Cook Incorporated 1997*, 3 pgs.
Westaby, S., Wound Care No. 11, *Nursing Times*, Jul. 21, 1982, 41-48.
White, R.A., et al., Vacuum-Assisted Closure Complicated by Erosion and Hemorrhage of the Anterior Tibial Artery, *Journal of Orthopaedic Trauma*, Jan. 2005, 19(1), 56-59, Abs. Cited in BlueSky internal email dtd. Nov. 9, 2005.
Williams, et al., Survey of the Use of Suction Drains in head and Neck Surgery and Analysis of Their Biomechanical Properties, *J. Otolaryngol.*, Feb. 2003, 32(1), 16-22, Abs. Downloaded from internet Nov. 30, 2003.
Windows on Medical Technology, Vacuum-Assisted Wound Closure for Chronic and Acute Wounds, *ECRI Health Technology Assessment Information Service*, Oct. 2000, 38, 1-21.
Witkowski, J.A. and Parish, L.C., Synthetic Dressings: Wound Healing in the '80s, *Hospital Therapy*, Nov. 1986, 75-84.
Wolthuis, Roger A., et al, "Physiological Effects of Locally Applied Reduced Pressure in Man," Physiological Reviews, Jul. 1974, pp. 566-595 vol. 54, No. 3, USA.
Wooding-Scott, Margaret, et.al, "No Wound is Too Big for Resourceful Nurses," RN, Dec. 1988, pp. 22-25, USA.
Worth, M.H. and H.W. Andersen, The Effectiveness of Bacterial Filtration in Vented Wound Drains, *Journ. of Surg. Research*, 1979, 27, 405-407.
Wu, P., et al., In Vitro Assessment of Water Vapour Transmission of Synthetic Wound Dressings, *Biomaterials*, 1995, 16(3), 171-175.
Wu, W.S., et al. Vacuum therapy as an intermediate phase in wound closure: a clinical experience, Eur J Past Surg (2000) 23: 174-177.
Yukhtin, V.I., et al., Surgical Treatment of Purulent Diseases of Soft tissues and Bones with the Use of Drainage-Bathing System, Content, Surg. No. 9 1997, Downloaded from internet, http://www.mediasphera.ru/surgery/97/9/e9-97ref.htm, 1 page.
Zamierowski, David S., Letter:"All Foam Sponges are not Equal in Vacuum Dressings," British Journal of Plastic Surgery, 1999, 52, 78-81, p. 79, United Kingdom.
Zhetimkarimov, D.S. and V.K. Ostrovsky, The Applied Significance of Anatomic Pecularities of Greater Momentum, Contents, Surg. No. 6, 1997, Downloaded from internet http://www.mediasphera.ru/surgery/97/6/e6-97ref.htm, 1 page.
Article Excerpt: Part III. Resolving Selected Clinical Dilemmas, 17-20.
Maitland and Mathieson, Suction Drainage, *Brit. J. Surg.*, Mar. 1970, 57(3), 195-197.
Orringer et al., "Management of Wounds in Patients with Complex Enterocutaneous Fistulas," Surgery, Gynecology, & Obstetrics, Jul. 1987, vol. 165, pp. 79-80.
Specific Inflammations, Diseases of the Skin, 549-550.
The Bier Treatment, *Brit. Journ. Nurs.*, Jun. 6, 1908, 452.
Tenta, L.T., et al., Suction Drainage of Wounds of the Head and Neck, Surg. Gyn. & Ob., Dec. 1989, 169, p. 558.
International Search Report of International Application No. PCT/GB00/04278 consisting of 2 pages, Feb. 22, 2001.
International Search Report of International Application No. PCT/NL2004/000565 consisting of 5 pages, Jul. 29, 2005.
International Search Report of International Application No. PCT/US2007/011278 consisting of 6 pages, May 11, 2006.
International Search Report of PCT/US2007/011321, International Filing Date May 10, 2007.
International Search Report of International Application No. PCT/GB00/01566 consisting of 2 pages, Sep. 25, 2000.
International Preliminary Report, International Application No. PCT/US2005/17225, dated Jul. 31, 2006, in 6 pages.
International Search Report, International Application No. PCT/US2005/17225, dated Oct. 4, 2005, in 1 page.
International Written Opinion, International Application No. PCT/US2005/17225, dated Oct. 4, 2005, in 4 pages.
Written Opinion of the International Search Report of PCT/US2007/011278 consisting of 7 pages, Dec. 11, 2007.

\* cited by examiner

REDUCED PRESSURE WOUND TREATMENT SYSTEM

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

This application is a divisional of U.S. application Ser. No. 12/856,460, filed Aug. 13, 2010, which is a continuation of U.S. application Ser. No. 11/095,859, filed Mar. 31, 2005, now U.S. Pat. No. 7,776,028, which claims the benefit of U.S. provisional application No. 60/559,726, filed on Apr. 5, 2004. The full disclosures of the aforementioned applications are hereby incorporated herein by reference.

BACKGROUND OF THE INVENTION

Field of the Invention

The present invention generally relates to treatment of wounds, and more specifically to an improved apparatus and method for treating a wound on a patient's body by applying reduced pressure to the body at the site of the wound. In this context, the terms "wound" and "body" are to be interpreted broadly, to include any wound that may be treated using reduced pressure.

Description of the Related Art

The treatment of open or chronic wounds that are too large to spontaneously close or otherwise fail to heal by means of applying reduced pressure to the site of the wound is well known in the art. One such system is disclosed in U.S. patent application Ser. No. 10/652,100, which was filed by one of the present inventors with the U.S. Patent and Trademark Office on Aug. 28, 2003. The disclosure of this U.S. patent application is incorporated herein by reference. Another system is disclosed in U.S. patent application Ser. No. 11/026,733, entitled "Improved Reduced Pressure Wound Treatment Appliance," which was filed by one of the present inventors with the U.S. Patent and Trademark Office on Dec. 30, 2004. The disclosure of this U.S. patent application is also incorporated herein by reference. Yet another system is disclosed in U.S. patent application Ser. No. 11/064,813, entitled "Improved Flexible Reduced Pressure Wound Treatment Appliance," which was filed by one of the present inventors with the U.S. Patent and Trademark Office on Feb. 24, 2005. The disclosure of this U.S. patent application is also incorporated herein by reference. And finally, the present inventors have filed a U.S. patent application (U.S. application Ser. No. 11/075,020, entitled "Enclosure-Based Reduced Pressure Treatment System") on Mar. 8, 2005, disclosing yet another system. The disclosure of this U.S. patent application is also incorporated herein by reference.

Reduced pressure wound treatment systems currently known in the art commonly involve placing a cover that is impermeable to liquids over the wound, using various means to seal the cover to the tissue of the patient surrounding the wound, and connecting a source of reduced pressure (such as a vacuum pump) to the cover in a manner so that an area of reduced pressure is created under the cover in the area of the wound. Of course, wounds that may be treated by using reduced pressure come in a variety of types, sizes and shapes. Thus, in order to treat a wide variety of wounds, it is necessary for health practitioners to have a number of different types and sizes of wound treatment covers on hand. This requirement, however, may cause undue expense in maintaining an inventory of such covers. In addition, this requirement may also cause shortages of storage space.

Therefore, there is a need for a single wound treatment device that can be used to treat a multitude of different types, sizes and shapes of wounds. This type of device, for example, would allow healthcare practitioners to maintain an inventory of fewer devices than they may have to maintain otherwise. This inventory reduction should also lower the cost of maintaining an inventory of wound treatment devices. In addition, an inventory of fewer devices should require less storage space. This reduction may also reduce facilities costs. There is also a need for a wound treatment device that is simple to modify, simple to apply to the patient's body, and simple to remove from the patient's body. In addition, there is a need for a reduced pressure treatment system that provides for efficient removal of any fluid aspirated from the wound. Finally, there is also a need for a reduced pressure treatment system that is relatively inexpensive, while meeting the needs described above.

SUMMARY OF THE INVENTION

The present invention is directed to a reduced pressure treatment appliance and methods that satisfy the needs described above. As described in greater detail below, they have many advantages over existing reduced pressure treatment apparatus and methods when used for their intended purpose, as well as novel features that result in a new reduced pressure treatment appliance and methods that are not anticipated, rendered obvious, suggested, or even implied by any of the prior art apparatus or methods, either alone or in any combination thereof.

In accordance with the present invention, a treatment appliance is provided for treating a wound on a body by applying reduced pressure (i.e., pressure that is below ambient atmospheric pressure) to the wound in a controlled manner for a selected time period in a manner that overcomes the disadvantages of currently existing apparatus. For example, the application of reduced pressure to a wound provides such benefits as faster healing, increased formation of granulation tissue, closure of chronic open wounds, reduction of bacterial density within wounds, inhibition of burn penetration, and enhancement of flap and graft attachment. Wounds that have exhibited positive response to treatment by the application of negative pressure include infected open wounds, decubitus ulcers, dehisced incisions, partial thickness burns, and various lesions to which flaps or grafts have been attached.

In one embodiment of a first version of the present invention, an appliance for treating a wound on a body is comprised of an overlay, sealing means to seal the overlay to the body, which are described in more detail below, and reduced pressure supply means, which are also described in more detail below. The overlay, which is sized to be placed over and enclose the wound, is further comprised of a top cup member and a secondary cup member. The top cup member is comprised of a top membrane portion and a top frame portion, in which the top frame portion is adjacent to and circumscribes the top membrane portion. The secondary cup member is comprised of a secondary membrane portion and a secondary frame portion, wherein the secondary membrane portion circumscribes and is attached to the top frame portion and the secondary frame portion is adjacent to and circumscribes the secondary membrane portion. The overlay and the sealing means allow reduced pressure to be maintained in the volume under the overlay at the site of the wound. The reduced pressure supply means operably connect the overlay to a reduced pressure supply source that provides a supply of reduced pressure to the overlay, so that the volume under the overlay at the site of the wound is supplied with reduced pressure by the reduced pressure supply source.

In other embodiments of this first version of the present invention, the top frame portion has a vertical displacement so that the secondary membrane portion and the top membrane portion do not lie within the same plane. In some of these embodiments, the overlay is further comprised of at least one vertical frame member extending along the contour of the surface of the overlay from the outside perimeter of the overlay to the outside perimeter of the top membrane portion. In some embodiments of this first version of the present invention, the overlay is approximately rectangular in shape. In other embodiments, the overlay is approximately elliptical in shape. In still other embodiments, the overlay is further comprised of a flexible lower membrane member that circumscribes and is attached to the secondary frame portion and the secondary frame portion has a vertical displacement so that the secondary membrane portion and the lower membrane member do not lie within the same plane. In some of these embodiments, the sealing means is comprised of the suction of the lower membrane member against the body, such suction being produced by the presence of reduced pressure in the volume under the overlay at the site of the wound. In other embodiments, the top cup member and the secondary cup member are comprised of a semi-rigid material and the top membrane portion and the secondary membrane portion each have a thickness less than the thickness of the top frame member and the secondary frame member. In still other embodiments, the top frame portion and the secondary frame portion are each comprised of semi-rigid materials, rigid materials, or combinations of such materials, and the top membrane portion and the secondary membrane portion are each comprised of semi-flexible materials, flexible materials, or combinations of such materials. In other embodiments, the sealing means may be comprised of an adhesive that is disposed between a portion of the outside perimeter of the overlay and the portion of the body adjacent to said portion of the outside perimeter of the overlay. In still other embodiments, the sealing means may be comprised of an adhesive tape that is disposed over a portion of the overlay and the portion of the body adjacent to said portion of the overlay. Further, in other embodiments, the appliance may further comprise a suction drain and suction drain connecting means to operably connect the reduced pressure supply means to the suction drain. In these embodiments, the suction drain extends from the reduced pressure supply means into the volume under the overlay at the site of the wound, and the suction drain is in fluid communication with the reduced pressure supply means so that reduced pressure is supplied by means of the suction drain to the volume under the overlay at the site of the wound. In yet other embodiments, the overlay may be further comprised of a pressure venting valve operably disposed on the overlay.

In other embodiments of this first version of the invention, the overlay may be comprised of a top cup member and at least two additional cup members. In these embodiments, the top cup member is comprised of a top membrane portion and a top frame portion and the top frame portion is adjacent to and circumscribes the top membrane portion. In addition, each of the at least two additional cup members is comprised of an additional membrane portion and an additional frame portion, wherein the additional membrane portion of one of the at least two additional cup members circumscribes and is attached to the top frame portion, and the additional frame portion of the one additional cup member is adjacent to and circumscribes the additional membrane portion of the one additional cup member. Further, the additional membrane portion of each additional cup member circumscribes and is attached to the frame portion of the previous additional cup member, and the additional frame portion of each additional cup member is adjacent to and circumscribes the additional membrane portion of said additional cup member. In these embodiments, the top cup member may generally have substantially the same structure, features, characteristics, and operation as the embodiments of the top cup member described above. Also in these embodiments, the at least two additional cup members may generally have substantially the same structure, features, characteristics, and operation as the embodiments of the secondary cup member described above.

In various embodiments of a second version of the present invention, the appliance for treating a wound on a body is comprised of an overlay, a seal to operably seal the overlay to the body, and reduced pressure supply means, which are described in more detail below. The overlay, which is sized to be placed over and enclose the wound, is further comprised of a top cup member and a secondary cup member. In these embodiments, the overlay is sized to be placed over and enclose the wound and is adapted to maintain reduced pressure in the volume under the overlay at the site of the wound. The seal and the reduced pressure supply means have substantially the same structure, features, characteristics and operation as the sealing means and the reduced pressure supply means, respectively, described above in connection with the first version of the present invention. Also in these embodiments, the overlay is comprised of a top cup member, a secondary cup member, and cup connecting means, which are described in more detail below, to removably connect the top cup member to the secondary cup member. In these embodiments, the top cup member is comprised of an interior top membrane portion, a top frame portion, and an exterior top membrane portion. The top frame portion is adjacent to and circumscribes the interior top membrane portion, and the exterior top membrane portion is adjacent to and circumscribes the top frame portion. The secondary cup member is comprised of an interior secondary membrane portion, a secondary frame portion, and an exterior secondary membrane portion. The interior secondary membrane portion is adjacent to a portion of and circumscribes the exterior top membrane portion, and the secondary frame portion is adjacent to and circumscribes the interior secondary membrane portion, and the exterior secondary membrane portion is adjacent to and circumscribes the secondary frame portion. In some of these embodiments, the top frame portion may have a vertical displacement so that the interior top membrane portion and the exterior top membrane portion do not lie within the same plane. The secondary frame portion may also have a vertical displacement so that the interior secondary membrane portion and the exterior secondary membrane portion do not lie within the same plane. In some of these embodiments, the top cup member may be further comprised of at least one vertical frame member extending along the contour of the surface of the top cup member from the outside perimeter of the top cup member to the outside perimeter of the interior top membrane portion. In addition, the secondary cup member may be further comprised of at least one vertical frame member extending along the contour of the surface of the secondary cup member from the outside perimeter of the secondary cup member to the inside perimeter of the secondary cup member. In some embodiments of this second version of the present invention, the cup connecting means may be comprised of an adhesive. In other embodiments, the cup connecting means may be comprised of snap connectors. In still other embodiments, the overlay may be approximately rectangular or approximately elliptical in shape. Except for the unique features described above, the appliance of this version of the present invention may generally have the same features and characteristics as described above in connection with the appliance of the first version of the present invention.

In other embodiments of this second version of the present invention, the overlay is comprised of a top cup member and at least two additional cup members. In these embodiments, the top cup member is comprised of an interior top membrane portion, a top frame portion, and an exterior top membrane portion. The top frame portion is adjacent to and circumscribes the interior top membrane portion, and the exterior top membrane portion is adjacent to and circumscribes the top frame portion. Each of the at least two additional cup members is comprised of an interior additional membrane portion, an additional frame portion, and an exterior additional membrane portion. The interior additional membrane portion of one of the at least two additional cup members circumscribes and is adjacent and removably attached to a portion of the exterior top membrane portion, and the additional frame portion of the one at least two additional cup members is adjacent to and circumscribes the interior additional membrane portion of the one at least two additional cup member, and the exterior additional membrane portion of the one at least two additional cup member is adjacent to and circumscribes the additional frame portion of the one at least two additional cup member. The interior additional membrane portion of each additional at least two cup members circumscribes and is adjacent and removably attached to a portion of the exterior membrane portion of the previous at least two additional cup member, and the additional frame portion of each additional at least two cup member is adjacent to and circumscribes the interior additional membrane portion of said at least two additional cup member, and the exterior additional membrane portion of said at least two additional cup member is adjacent to and circumscribes the additional frame portion of said at least two additional cup member. In these embodiments, the top cup member may generally have substantially the same structure, features, characteristics, and operation as the embodiments of the top cup member described above in connection with the second version of the present invention. Also in these embodiments, the at least two additional cup members may generally have substantially the same structure, features, characteristics, and operation as the embodiments of the secondary cup member described above in connection with the second version of the present invention.

In a third version of the present invention, an appliance for administering reduced pressure treatment to a wound on a body is comprised of a treatment device and a vacuum system. In various embodiments of this third version of the invention, the treatment device is also comprised of an overlay and sealing means, which may have substantially the same structure, features, characteristics and operation as the overlay and sealing means, respectively, described above in connection with the first and second versions of the present invention. In this third version of the invention, the vacuum system is further comprised of a reduced pressure supply source that provides a supply of reduced pressure and reduced pressure supply means (which are described in more detail below) to operably connect the treatment device to the reduced pressure supply source, so that the volume under the treatment device at the site of the wound is supplied with reduced pressure by the reduced pressure supply source. In various embodiments of this third version of the invention, the reduced pressure supply means may generally have substantially the same structure, features, characteristics and operation as the reduced pressure supply means described above in connection with the first and second versions of the invention.

In some embodiments of this third version of the invention, the reduced pressure supply source is comprised of a vacuum pump. In some of these embodiments, the reduced pressure supply source further comprises a control system for the vacuum pump, wherein the control system may control at least the level of suction produced by the vacuum pump or the rate of fluid flow produced by the vacuum pump, or any combination of rate of suction and rate of fluid flow of the vacuum pump. In other embodiments, the reduced pressure supply source further comprises a filter operably positioned between the vacuum pump and the reduced pressure supply means. In these embodiments, the filter prevents the venting of and contamination of the vacuum pump by micro-organisms or fluids (or both) aspirated from the wound. In yet other embodiments, the vacuum pump is comprised of a portable vacuum pump. In still other embodiments of this third version of the invention, the reduced pressure supply means is comprised of flexible tubing. In other embodiments, the reduced pressure supply means is further comprised of a collection system that is operably positioned between the treatment device and the reduced pressure supply source. In some of these embodiments, the collection system comprises a container to receive and hold fluid aspirated from the wound and pressure halting means to halt the application of reduced pressure to the wound when the fluid in the container exceeds a predetermined amount. In other embodiments of this third version of the invention, the reduced pressure under the overlay at the site of the wound is in the range from approximately 20 mm of Hg below atmospheric pressure to approximately 125 mm of Hg below atmospheric pressure. In yet other embodiments, the reduced pressure is applied in a cyclic nature, the cyclic nature providing alternating time periods of application of reduced pressure and without application of reduced pressure.

In a fourth version of the present invention, an appliance for administering reduced pressure treatment to a wound on a body is comprised of a treatment device and a vacuum system. In various embodiments of this fourth version of the invention, the treatment device is also comprised of an overlay and sealing means, which may have substantially the same structure, features, characteristics and operation as the overlay and sealing means, respectively, described above in connection with the first and second versions of the present invention. In the various embodiments of this fourth version of the invention, the vacuum system is comprised of a suction bulb, which may (but not necessarily) provide a source of reduced pressure, and reduced pressure supply means, which are described in more detail below, to operably connect the overlay to the suction bulb, so that the site of the wound in the volume under the overlay may be supplied with reduced pressure by the suction bulb. In some embodiments of this fourth version of the invention, the suction bulb is further comprised of an inlet port and an outlet port, wherein the inlet port is operably connected to the reduced pressure supply means, and the vacuum system further comprises an exhaust tubing member operably connected to the outlet port. In some of these embodiments, the vacuum system further comprises an exhaust control valve operably connected to the exhaust tubing member. In other embodiments, the vacuum system is further comprised of a filter operably connected to the exhaust tubing member, which prevents the venting of micro-organisms or fluids (or both) aspirated from the wound. In yet other embodiments, the vacuum system is further comprised of a supplemental vacuum system that is operably connected to the exhaust tubing member. In these embodiments, the supplemental vacuum system may generally have substantially the same structure, features, characteristics and operation as the vacuum system described above in connection with the third version of the invention.

In some embodiments of another aspect of the third and fourth versions of the invention, the treatment device is further comprised of wound packing means, which are described in more detail below, that are positioned within the wound. In these embodiments, the overlay is placed over and encloses the wound and the wound packing means. In some embodiments, the wound packing means is comprised of absorbent dressings, antiseptic dressings, nonadherent dressings, water dressings, or combinations of such dressings. In other embodiments, the wound packing means is comprised of an absorbable matrix adapted to encourage growth of the tissue in the area of the wound under the overlay into the matrix. The absorbable matrix is constructed of an absorbable material that is absorbed into the epithelial and subcutaneous tissue in the wound as the wound heals. In other embodiments of this aspect of the invention, the treatment appliance further comprises a suction drain and suction drain connecting means, which are described in more detail below. The suction drain connecting means operably connect the reduced pressure supply means to the suction drain so that the suction drain is in fluid communication with the reduced pressure supply means and reduced pressure is supplied by means of the suction drain to the volume under the overlay at the site of the wound. In these embodiments, the suction drain extends from the reduced pressure supply means into the volume under the overlay in the area of the wound. In some of these embodiments, the suction drain is further comprised of a distal end portion and the distal end portion has at least one perforation in the surface thereof. In some of these embodiments, the distal end portion of the suction drain is positioned within the interior volume of the wound packing means.

A fifth version of the present invention discloses a method of treating a wound. In one embodiment of this fifth version of the invention, the method comprises the following steps. First, an overlay is positioned on the body over the wound, wherein the overlay may have substantially the same structure, features, characteristics and operation as the overlay described above in connection with the first and second versions of the invention. Second, the overlay is operably sealed to the body so that reduced pressure may be maintained in the volume under the overlay at the site of the wound. Third, the overlay is operably connected with a vacuum system for producing reduced pressure in the volume under the overlay at the site of the wound. Fourth, the reduced pressure is maintained until the wound has progressed toward a selected stage of healing. In other embodiments of this fifth version of the invention, the method further comprises the step of detaching at least one additional cup member of the overlay so that the overlay may be sized to cover a smaller area of the body surrounding the wound, such step being performed prior to positioning the overlay on the body over the wound. In still other embodiments, the method further comprises the step of cutting away a portion of the overlay so that the overlay is sized to cover a smaller area of the body surrounding the wound, such step being performed prior to positioning the overlay on the body over the wound. In yet other embodiments, the vacuum system is comprised of a suction bulb and the method further comprises the step of squeezing the suction bulb to reduce its volume and then releasing the suction bulb, so that reduced pressure is produced in the volume under the overlay at the site of the wound. In other embodiments of this fifth version of the invention, the reduced pressure under the overlay at the site of the wound is in the range from approximately 20 mm of Hg below atmospheric pressure to approximately 125 mm of Hg below atmospheric pressure. In still other embodiments of this fifth version of the invention, the reduced pressure is applied in a cyclic nature, the cyclic nature providing alternating time periods of application of reduced pressure and without application of reduced pressure. In other embodiments, the method further comprises the step of placing wound packing means between the wound and the overlay, such step being performed prior to positioning the enclosure over the wound. It is to be noted that in various other embodiments, the steps described above may be performed in a different order than that presented.

The present invention therefore meets the needs discussed above in the Background section. For example, the overlay of the present invention may be modified so that it is appropriate for treatment of a variety of different types, sizes and shapes of wounds. The size of the overlay may be adjusted by removing one or more of the outer cup members. The shape of the overlay may be modified by cutting away different portions of the overlay. As a result, healthcare practitioners may be required to purchase fewer overlays than they would be required to purchase if a variety of other wound treatment devices were required. This would apparently reduce costs of facilities, as well as costs of maintaining inventory of wound treatment devices.

The appliance of the present invention is also simple to modify, simple to apply to the patient's body, and simple to remove from the patient's body. In addition, the appliance of the present invention provides for efficient removal of any fluid aspirated from the wound. Finally, the appliance should be relatively inexpensive, while meeting the needs described above.

There has thus been outlined, rather broadly, the more primary features of the present invention. There are additional features that are also included in the various embodiments of the invention that are described hereinafter and that form the subject matter of the claims appended hereto. In this respect, it is to be understood that the invention is not limited in its application to the details of construction and to the arrangements of the components set forth in the following description or illustrated in the following drawings. This invention may be embodied in the form illustrated in the accompanying drawings, but the drawings are illustrative only and changes may be made in the specific construction illustrated and described within the scope of the appended claims. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

The foregoing summary, as well as the following detailed description of the preferred embodiments of the present invention, will be better understood when read in conjunction with the appended drawings, in which.

DETAILED DESCRIPTION OF THE PREFERRED EMBODIMENT

Figure 1:
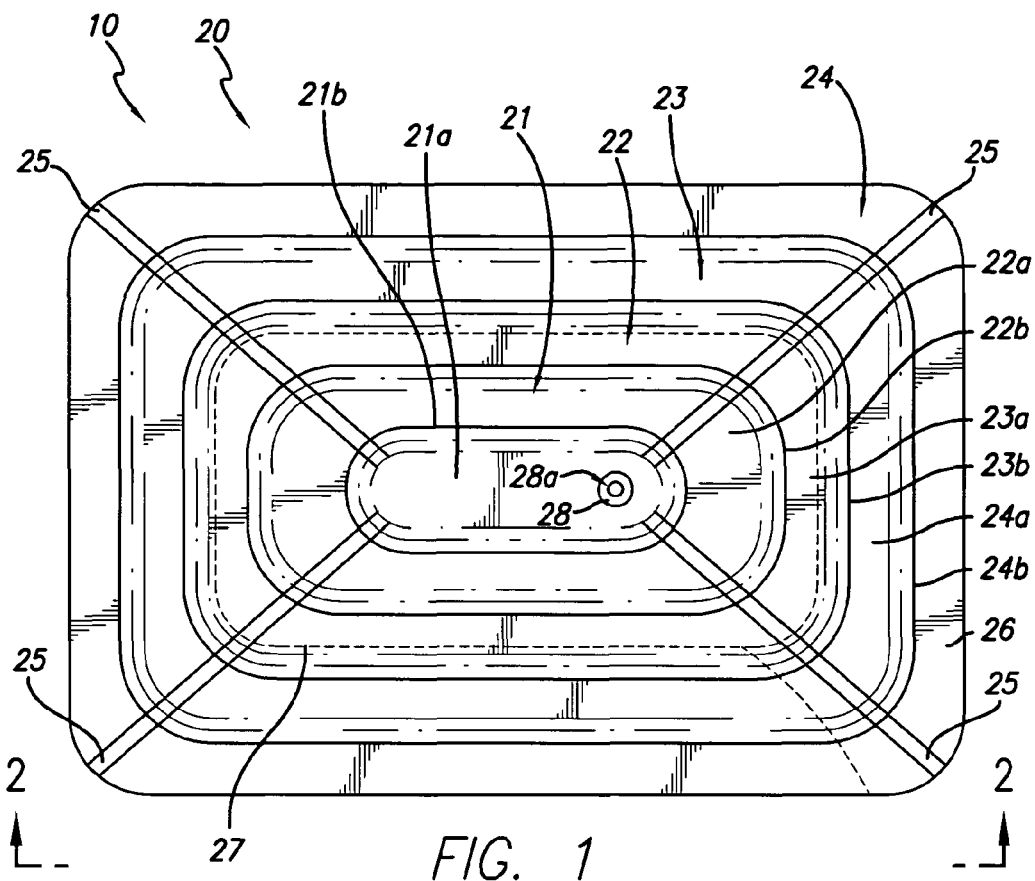
FIG. 1 is a plan view of an embodiment of an overlay comprising the present invention, as such overlay would appear from above the body of a patient while the overlay is positioned on the body.

In accordance with the present invention, a treatment appliance is provided for treating a wound by applying reduced pressure (i.e., pressure that is below ambient atmospheric pressure) to the wound in a controlled manner for a selected time period in a manner that overcomes the disadvantages of currently existing apparatus. One embodiment of a first version of the invention is the treatment appliance 10, which is comprised of an overlay 20, illustrated in FIG. 1 (a plan view of the overlay 20) and FIG. 2 (an elevation view of the overlay 20), in each case as the overlay 20 would appear when applied to a wound (not shown). In this embodiment, the overlay 20 is comprised of a top cup member 21, a secondary cup member 22, a first additional cup member 23, a second additional cup member 24, sealing means to seal the overlay 20 to the body (not illustrated), which are described in more detail below, and reduced pressure supply means, which are also described in more detail below. The overlay 20 is generally sized to be placed over and enclose the wound to be treated. The overlay 20 and the sealing means (described in more detail below) allow reduced pressure to be maintained in the volume under the overlay 20 at the site of the wound to be treated, as described in more detail below. The reduced pressure supply means (not illustrated) are used to operably connect the overlay 20 to a reduced pressure supply source (also not illustrated) in a manner so that the reduced pressure supply source provides a supply of reduced pressure to the overlay 20, so that the volume under the overlay 20 at the site of the wound may be maintained at reduced pressure.

Figure 2:
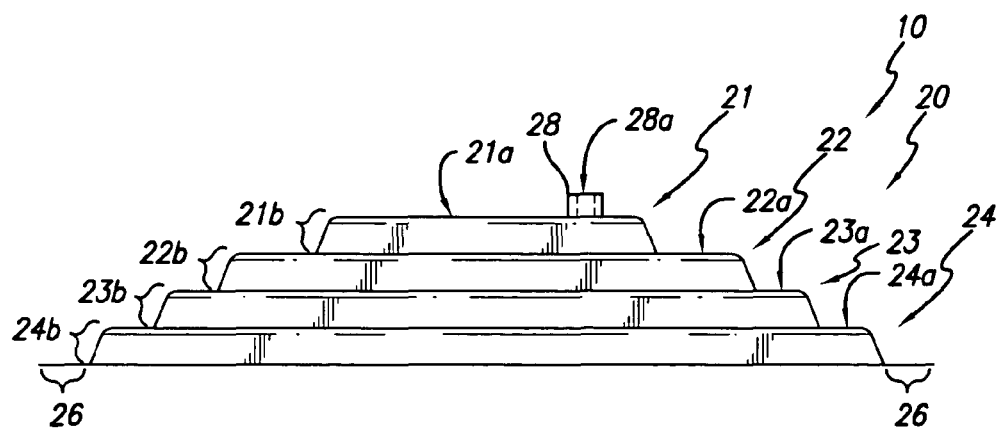
FIG. 2 is an elevation view of the embodiment of the overlay illustrated in FIG. 1, as taken along the lines 2-2 of FIG. 1.
Figure 6:
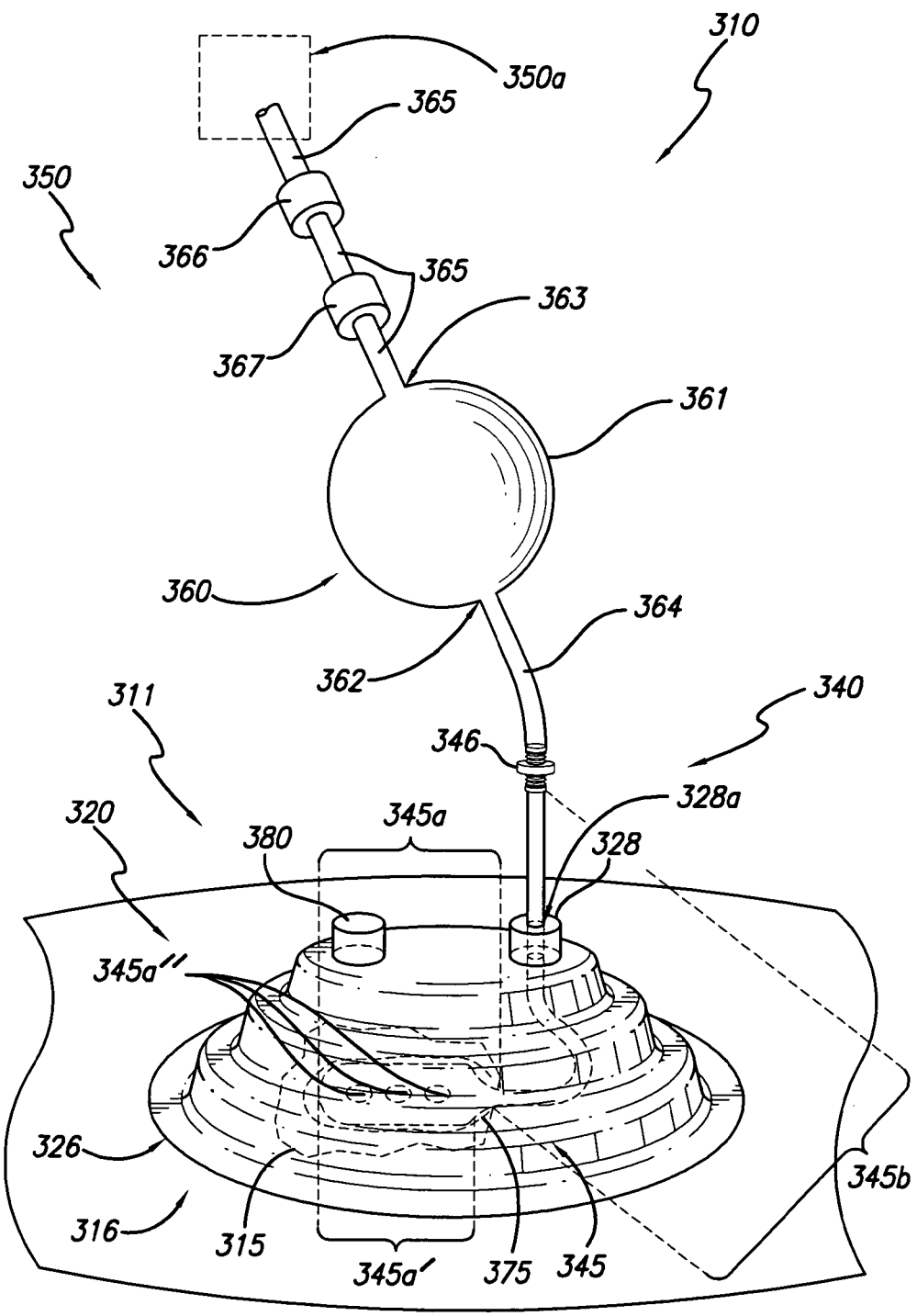
FIG. 6 is a view of an embodiment of a treatment appliance comprising the present invention, in which an embodiment of a treatment device, shown in perspective view from the side of and above the treatment device, is positioned over a wound on a body, and in which an embodiment of a vacuum system, shown in elevational view, provides reduced pressure within the volume under an overlay comprising the treatment device.

The overlay 20 illustrated in FIG. 1 and FIG. 2 is in its natural shape, as it exists prior to being applied to a patient for treatment of the wound. In the embodiment illustrated in FIG. 1 and FIG. 2, the overlay 20, when viewed from above the overlay 20 as it would appear while placed over the wound, is shaped approximately as a rectangle with rounded corners. In other embodiments of this first version of the present invention, the overlay 20 may be of almost any shape or combination of shapes. For example, as illustrated in FIG. 6, the overlay 320 may be approximately ellipsoidal in shape. In the illustrated embodiment, the top cup member 21 is comprised of a top membrane portion 21a and a top frame portion 21b, and the secondary cup member 22 is comprised of a secondary membrane portion 22a and a secondary frame portion 22b. Similarly, the first additional cup member 23 is comprised of a first additional membrane portion 23a and a first additional frame portion 23b, and the second additional cup member 24 is comprised of a second additional membrane portion 24a and a second additional frame portion 24b. Thus, in the illustrated embodiment, the top frame portion 21b is adjacent to and circumscribes the top membrane portion 21a, the secondary membrane portion 22a is adjacent to and circumscribes the top frame portion 21b, the secondary frame portion 22b is adjacent to and circumscribes the secondary membrane portion 22a, the first additional membrane portion 23a is adjacent to and circumscribes the secondary frame portion 22b, the first additional frame portion 23b is adjacent to and circumscribes the first additional membrane portion 23a, the second additional membrane portion 24a is adjacent to and circumscribes the first additional frame portion 23b, and the second additional frame portion 24b is adjacent to and circumscribes the second additional membrane portion 24a. It is to be noted that the top cup member 21, the secondary cup member 22, the first additional cup member 23, and the second additional cup member 24 may be fabricated as a single piece or they may be attached together by any appropriate means, such as welding, fusing, fasteners or other means or combinations of all such means. It is also to be noted that in the illustrated embodiment the top membrane portion 21a, the secondary membrane portion 22a, the first additional membrane portion 23a, and the second additional membrane portion 24a are each approximately flat and generally define a plane. In addition, in this embodiment, the top frame portion 21b, the secondary frame portion 22b, the first additional frame portion 23b, and the second additional frame portion 24b each have a vertical displacement relative to the adjacent membrane portions 21a, 22a, 23a, 24a, respectively. As a result, the top membrane portion 21a, the secondary membrane portion 22a, the first additional membrane portion 23a, and the second additional membrane portion 24a are each in a different plane, so that the second additional membrane portion 24a is on a plane closest to the body, the first additional membrane portion 23a is on a plane higher than the second additional membrane portion 24a, the secondary membrane portion 22a is on a plane higher than the first additional membrane portion 23a, and the top membrane portion 21a is on a higher plane than the secondary membrane portion 22a. In other embodiments, the top membrane portion 21a, the secondary membrane portion 22a, the first additional membrane portion 23a, the second additional membrane portion 24a, or any combination of the same may not be flat or define a plane. Instead, they may be of almost any shape or combination of shapes. For example, in other embodiments, the top membrane portion 21a, the secondary membrane portion 22a, the first additional membrane portion 23a, the second additional membrane portion 24a, or any combination of the same may have a curved surface that may or may not parallel the surface of any other membrane portion 21a, 22a, 23a, 24a. In addition, in other embodiments, the top frame portion 21b, the secondary frame portion 22b, the first additional frame portion 23b, the second additional frame portion 24b, or any combination of the same may be of almost any shape or combination of shapes. For example, the top frame portion 21b, the secondary frame portion 22b, the first additional frame portion 23b, the second additional frame portion 24b, or any combination of the same may have a curvature in an orientation different from that illustrated in FIG. 2. It is also to be noted that in other embodiments the top cup member 21, the secondary cup member 22, the first additional cup member 23, and the second additional cup member 24 may be of different sizes and shapes relative to one another. For example, in some embodiments, the top cup member 21 and the secondary cup member 22 may be relatively close in size and shape, while the first additional cup member 23 and the second additional cup member 24 may be relatively close in size, but not in shape, and both may be of a size and shape substantially different from that of the top cup member 21 and the secondary cup member 22. Thus, the top cup member 21 may be circular in shape and have a diameter of approximately 2 inches, and the secondary cup member 22 may also be circular in shape and have a diameter of 2½ inches. Further, in this example, the first additional cup member 23 may be approximately elliptical in shape and have a major diameter of approximately 5¼ inches and a minor diameter of approximately 4 inches, and the second additional cup member 24 may be approximately rectangular in shape with a width of approximately 4¼ inches and a length of approximately 6 inches. Further still, the vertical displacement of the top frame portion 21b and the second additional frame portion 24b may be approximately ¼, while the vertical displacement of the secondary frame portion 22b and the first additional frame portion 23b may each be approximately ½ inch. Thus, almost any combination of shapes and sizes is possible for the overlay 20 and its component parts. As another example, the cup members 21, 22, 23, 24 may be polygonal, any combination of curved shapes, or any combination of all of such shapes, when viewed from above the overlay 20. The preferred shape and size of the overlay 20, as well as the size and shape of the cup members 21, 22, 23, 24 comprising it, are dependent upon the materials comprising the overlay 20, the thickness of the overlay 20, the nature of the wound to be treated, the size, shape and contour of the portion of the body to be covered by the overlay 20, the magnitude of the reduced pressure to be maintained under the overlay 20, the individual preferences of the user of the overlay 20, and other factors related to the sealing means, reduced pressure supply means, and use of a suction drain (if any), as described in more detail below. In addition, in the illustrated embodiment, there are also four vertical frame members 25, which generally follow the contour of the surface of the overlay 20. In other embodiments, there may be fewer or more vertical frame members 25 and the vertical frame members 25 may be of almost any shape and size. In yet other embodiments, there may not be any vertical frame members 25. In still other embodiments, as illustrated in FIG. 2, the overlay 20 may also be comprised of a lower membrane member 26, which is adjacent to and circumscribes the second frame member 24b. In these embodiments, as described in more detail below, the lower membrane member 26 may be used as a part of the sealing means (which is also described in more detail below) to operably seal the overlay 20 to the body. It is to be noted that the lower membrane member 26 and the second additional cup member 24 may be fabricated as a single piece or they may be attached together by any appropriate means, such as welding, fusing, fasteners or other means or combinations of all such means.

In the embodiment of the present invention illustrated in FIG. 1 and FIG. 2, the top frame portion 21b, the secondary frame portion 22b, the first additional frame portion 23b, and the second additional frame portion 24b are each constructed of a material that is rigid enough to support the overlay 20 away from the wound. In addition, the vertical frame members 25 are each constructed of a material that is rigid enough to support the overlay 20 away from the wound. Further, the top membrane portion 21a, the secondary membrane portion 22a, the first additional membrane portion 23a, and the second additional membrane portion 24a are each constructed of a material that may be supported away from the wound by the frame portions 21b, 22b, 23b, 24b or the vertical frame members 25 or by any or all of the same. It should be noted, however, that the membrane portions 21a, 22a, 23a, 24a may be constructed of a flexible material, as well as a semi-rigid material or even a rigid material. In each case, the membrane portions 21a, 22a, 23a, 24a, the frame portions 21b, 22b, 23b, 24b, and the vertical frame members 25 are constructed of materials and in a manner so that the overlay 20 can be reduced to a smaller size when desired by the user of the overlay 20. For example, as illustrated in FIG. 1, if the user of the overlay 20 determines that only the top cup member 21 and the secondary cup member 22 are required for treatment of a wound, the user may use scissors, a knife or other instrument to cut into the overlay 20 along the dotted-line 27. After making this cut, the user may discard the first additional cup member 23 and the second additional cup member 24 and retain the top cup member 21 and the secondary cup member 22 for treatment of the wound. It is to be noted that the cut may be made in almost any shape along almost any line or lines, at the discretion of the user of the overlay 20. Thus, after making the cut, the overlay 20 may be of almost any shape and size within the scope of the original size and shape of the overlay 20. The preferred shape and size of the overlay 20 after making the cut is generally dependent upon the same factors governing the size and shape of the pre-cut overlay 20, as described in more detail above in the immediately preceding paragraph. In the various embodiments of this first version of the invention, the frame portions 21b, 22b, 23b, 24b and the vertical frame members 25 of the overlay 20 may be comprised of almost any rigid or semi-rigid medical grade material that is currently known in the art or that may be developed in the art in the future, as long as such material is liquid-impermeable, suitable for purposes of wound treatment (e.g., can be sterilized and does not absorb significant amounts of fluids, such as wound exudate), is capable of supporting the overlay 20 away from the wound, and is capable of being cut in the manner described above with a reasonable amount of effort. For example, the frame portions 21b, 22b, 23b, 24b and the vertical frame members 25 of the overlay 20 may each be comprised of rubber (including neoprene), metal, wood, paper, ceramic, or rigid or semi-rigid polymer materials, such as polypropylene, polyvinyl chloride, silicone, silicone blends, or other polymers or combinations of all such polymers. In contrast, and also for example, the membrane portions 21a, 22a, 23a, 24a may be comprised of rubber (including neoprene) or rigid, semi-rigid, or flexible polymer materials, such as paper, polypropylene, polyvinyl chloride, silicone, silicone blends, polyurethane or similar polymers, or combinations of all such materials. It is to be noted that in various embodiments of this first version of the invention, the overlay 20 may be constructed in whole or in part of gas-permeable materials, allowing limited amounts of oxygen to penetrate the overlay 20 so that the portion of the body under the overlay 20 can "breathe." In some embodiments, all portions of the overlay 20 are preferably constructed of one type of semi-rigid material, such as a silicone blend. In some of these embodiments, the thickness of various portions of the overlay 20 may vary in order to vary the rigidity of the portions and the ability to cut them in the manner described above. For example, in embodiments of the overlay 20 illustrated in FIG. 1 and FIG. 2 where the overlay 20 is constructed entirely of a silicone blend, the frame portions 21b, 22b, 23b, 24b and the vertical frame members 25 of the overlay 20 may have an approximate thickness of 1/16 inches, and the membrane portions 21a, 22a, 23a, 24a may have an approximate thickness of 1/32 inches. In other embodiments, the overlay 20 may be constructed of more than one material. For example, the frame portions 21b, 22b, 23b, 24b and the vertical frame members 25 of the overlay 20 may be comprised of polyvinyl chloride, and the membrane portions 21a, 22a, 23a, 24a may be comprised of silicone. This may be the case where it is desirable for the portions of the overlay 20 to have the same thickness. Thus, for the overlay 20 illustrated in FIG. 1 and FIG. 2 having a uniform thickness of approximately 1/16 inches, the frame portions 21b, 22b, 23b, 24b and the vertical frame members 25 of the overlay 20 may be comprised of polyvinyl chloride, and the membrane portions 21a, 22a, 23a, 24a may be comprised of silicone. The preferred thickness of the overlay 20 and its various component parts is dependent upon the size and shape of the overlay 20, the size, shape and contour of the portion of the body to be covered by the overlay 20, the magnitude of the reduced pressure to be maintained under the overlay 20, the materials comprising the overlay 20, and the individual preferences of the user of the overlay 20. For example, in the embodiment illustrated in FIG. 1 and FIG. 2, for an overlay 20 constructed entirely of a silicone blend, having the illustrated shape, being of a uniform thickness, and having an approximate length of 8 inches and an approximate width of 6 inches, the preferred thickness of the overlay 20 is in the range from 1/32 inches to 3/8 inches. It is to be noted that in other embodiments the thickness of the various portions of the overlay 20 may vary from embodiment to embodiment, as well as from portion to portion of the overlay 20. Generally, the overlay 20 of the illustrated embodiment may be constructed using any suitable means currently known in the art or that may be developed in the art in the future. For example, an overlay 20 constructed entirely of a silicone blend may be manufactured by means of injection molding. As another example, embodiments of overlays 20 constructed of different types of materials may be constructed by fusing or welding the portions of the overlay 20 together.

In some embodiments of this first version of the present invention, as illustrated in FIG. 1 and FIG. 2, the overlay 20 further comprises a port 28. The port 28 is adapted to be of a size and shape so that the reduced pressure supply means may be operably connected to the overlay 20 by means of the port 28. When the port 28 is operably connected to the reduced pressure supply means, reduced pressure may be supplied to the volume under the overlay 20 at the site of the wound to be treated. Although the port 28 is positioned at a location near one end of the top membrane portion 21a of the enclosure 20 in the embodiment illustrated in FIG. 1 and FIG. 2, the port 28 may be located at other positions on the overlay 20 in other embodiments, as long as the port 28 does not adversely affect the ability of the overlay 20 to make an operable seal with the surface of the body adjacent to the overlay 20, as described in more detail below. For example, the port 28 may not be located too close to the outside edge of the overlay 20 because an operable seal with the surface of the body is typically formed at that location. Although the port 28 may be constructed of a material different from the material comprising the remainder of the overlay 20 in various embodiments of the invention, the port 28 is preferably constructed from the same material comprising the top cup member 21 of the overlay 20. In the embodiments of the overlay 20 illustrated in FIG. 1 and FIG. 2 the port 28 is generally cylindrical in shape and is further comprised of an approximately cylindrical channel 28a that extends from the top of the port 28 to the bottom of the port 28. The port 28 of this embodiment is thus able to receive a vacuum system or reduced pressure supply means, which are described in more detail below, adapted to be connected to this shape of port 28 and channel 28a. In other embodiments of this first version of the invention, the port 28 or the channel 28a or both may have different shapes and configurations as may be desired to adapt and connect the port 28 and the channel 28a to the vacuum system or reduced pressure supply means, which are described in more detail below. In some of the embodiments comprising a port 28, the overlay 20 is further comprised of flow control means (not shown) that are operably connected to the port 28. The flow control means permit fluids to flow from the volume under the overlay 20 at the site of the wound through the port 28 to a volume (such as the reduced pressure supply means) outside the overlay 20, but not in the opposite direction. In some of these embodiments, the flow control means may be a one-way valve that is located within the channel 28a in the port 28. Such valves are well known in the relevant art. In other embodiments of this first version of the invention, a means of connecting the overlay 20 to the reduced pressure supply means (described in more detail below) may be located on the overlay 20 in lieu of or in conjunction with the port 28. For example, in some embodiments, the port 28 may be combined with a variable descending diameter adapter (commonly referred to as a "Christmas tree" adapter).

Figure 3:
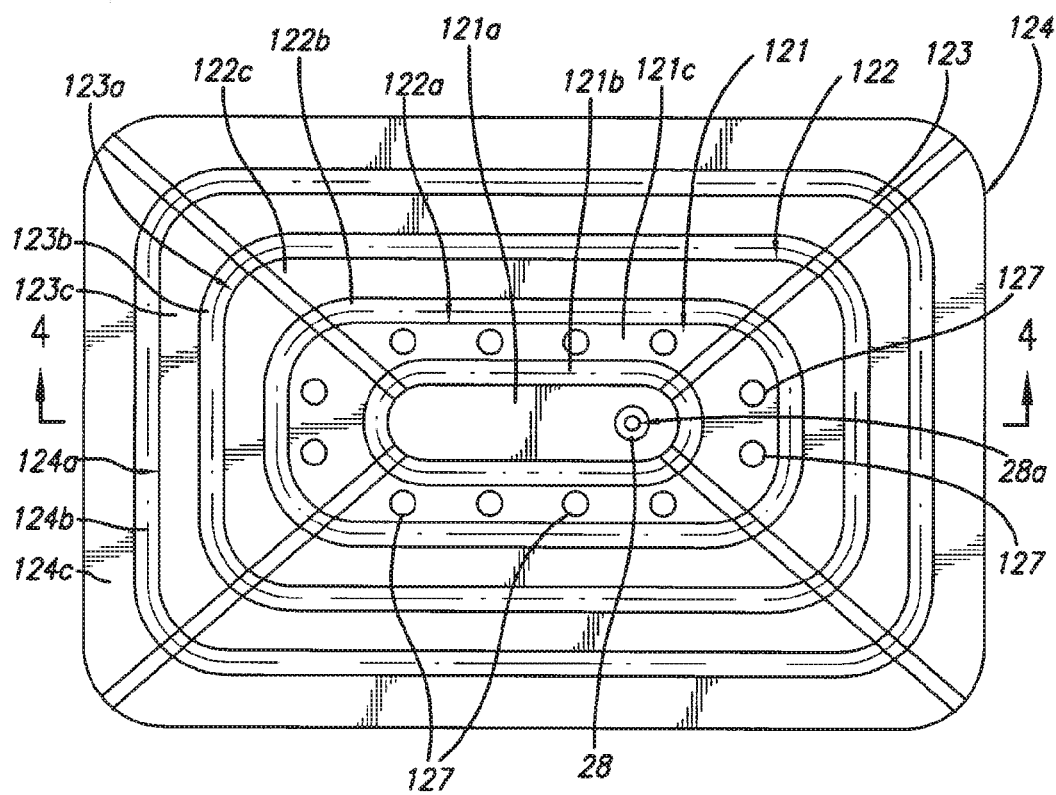
FIG. 3 is a plan view of another embodiment of an overlay comprising the present invention, as such overlay would appear from above the body of a patient while the overlay is positioned on the body.
Figure 4:
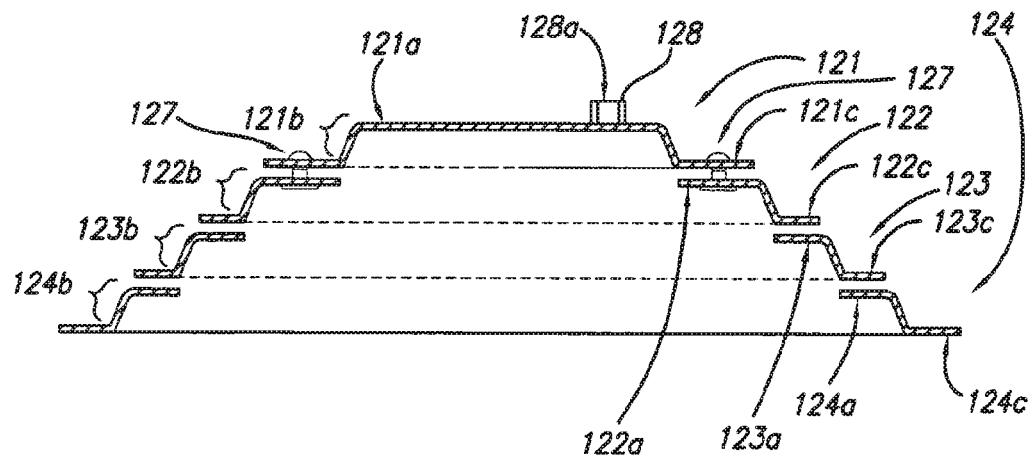
FIG. 4 is a cross-sectional elevation view of the embodiment of the overlay illustrated in FIG. 3, as taken along the lines 4-4 of FIG. 3.

An embodiment of a second version of the present invention is illustrated in FIG. 3 and FIG. 4. In this embodiment, the overlay 120 is also in its natural shape, as it exists prior to being applied to a patient for treatment of a wound (not shown). Also in this embodiment, the overlay 120 is comprised of a top cup member 121, a secondary cup member 122, a first additional cup member 123, a second additional cup member 124, sealing means to seal the overlay 120 to the body (not illustrated), which are described in more detail below, and reduced pressure supply means, which are also described in more detail below. The overlay 120 is generally sized to be placed over and enclose the wound to be treated in the same manner as the overlay 20 illustrated and described above in connection with FIG. 1 and FIG. 2. In addition, the sealing means and the reduced pressure supply means (which are described in more detail below) are substantially the same as for the overlay 20 illustrated and described above in connection with FIG. 1 and FIG. 2. In the embodiment illustrated in FIG. 3 and FIG. 4, the overlay 120, when viewed from above the overlay 120 as it would appear while placed over the wound, is shaped approximately as a rectangle with rounded corners. In other embodiments, the overlay 120 and its component parts may also have any of the sizes, shapes and combinations of sizes and shapes as the overlay 20 and its component parts illustrated and described above in connection with FIG. 1 and FIG. 2. In the illustrated embodiment, the top cup member 121 is comprised of an interior top membrane portion 121*a*, a top frame portion 121*b*, and an exterior top membrane portion 121*c*. The top frame portion 121*b* is adjacent to and circumscribes the interior top membrane portion 121*a*, and the exterior top membrane portion 121*c* is adjacent to and circumscribes the top frame portion 121*b*. Similarly, the secondary cup member 122 is comprised of an interior secondary membrane portion 122*a*, a secondary frame portion 122*b*, and an exterior secondary membrane portion 122*c*. The secondary frame portion 122*b* is adjacent to and circumscribes the interior secondary membrane portion 122*a*, and the exterior secondary membrane portion 122*c* is adjacent to and circumscribes the secondary frame portion 122*b*. Further, the first additional cup member 123 is comprised of an interior first additional membrane portion 123*a*, a first additional frame portion 123*b*, and an exterior first additional membrane portion 123*a*. The first additional frame portion 123*b* is adjacent to and circumscribes the interior first additional membrane portion 123*a*, and the exterior first additional membrane portion 123*c* is adjacent to and circumscribes the first additional frame portion 123*b*. Further still, the second additional cup member 124 is comprised of an interior second additional membrane portion 124*a*, a second additional frame portion 124*b*, and an exterior second additional membrane portion 124*c*. The second additional frame portion 124*b* is adjacent to and circumscribes the interior second additional membrane portion 124*a*, and the exterior first additional membrane portion 124*c* is adjacent to and circumscribes the first additional frame portion 124*b*. In the illustrated embodiment, a portion of the exterior top membrane portion 121*c* overlaps and is adjacent to a portion of the interior secondary membrane portion 122*a*, a portion of the exterior secondary membrane portion 122*c* overlaps and is adjacent to a portion of the interior first additional membrane portion 123*a*, and a portion of the exterior first additional membrane portion 123*c* overlaps and is adjacent to a portion of the interior second additional membrane portion 124*a*. The overlapping portions are removably connected together using cup connecting means, which permit the cup members 121, 122, 123, 124 to be separated from one another when the user of the overlay 120 desires an overlay 120 that is of a shape or size different from that of the original shape and size of the overlay 120. Thus, instead of cutting the overlay 120, as may be done with the embodiment of the overlay 20 illustrated and described above in connection with FIG. 1 and FIG. 2, the user of the overlay 120 merely separates the desired cup member 121, 122, 123, 124 or cup members 121, 122, 123, 124 from the remaining cup members 121, 122, 123, 124. It is to be noted, however, that the user of the overlay 120 may still cut portions of the overlay 120 away to modify the shape or size of the overlay 120. The cup connecting means may be almost any means currently known in the relevant art or developed in the relevant art in the future that are suitable for connecting the cup members 121, 122, 123, 124 together in the manner described above. In the illustrated embodiment, such means is comprised of a plurality of snapping connectors 127, which are well known in the relevant art and are used to connect the top cup member 121 to the secondary cup member 122. Also in the illustrated embodiment, such means is comprised of an adhesive that is disposed between the overlapping membrane portions 122*c*, 123*a* and 123*c*, 124*a* that permits the cup members 122, 123, 124 to be peeled apart when the user desires. Such adhesives are also well known in the relevant art. In yet other embodiments, such means may include hook and loop fasteners (such as VELCRO), adhesive tape, a bead-groove locking system (such as that used on polymer sandwich and refrigerator bags), and other connecting means and combinations of all such means. It is also to be noted that the cup connecting means must allow for an approximately hermetic seal between the cup members 121, 122, 123, 124. For example, the seal between the cup members 121, 122, 123, 124 must be sufficiently airtight and liquid-tight so that reduced pressure may be maintained in the volume under the overlay 120 at the site of the wound. The seal need not, however, be completely airtight and liquid-tight.

In the same manner as illustrated and described above with respect to the cup members 21, 22, 23, 24 comprising the overlay 20 of FIG. 1 and FIG. 2, the cup members 121, 122, 123, 124 comprising the overlay 120 may be of various shapes and sizes, as long as the shapes and sizes permit the cup members 121, 122, 123, 124 to be removably connected in the manner described above. In addition, in the embodiment of this second version of the present invention illustrated in FIG. 3 and FIG. 4, the top frame portion 121*b*, the secondary frame portion 122*b*, the first additional frame portion 123*b*, and the second additional frame portion 124*b* are each constructed of a material that is rigid enough to support the overlay 120 away from the wound. In addition, in some embodiments, the overlay 120 may also comprise vertical frame members (not shown), which may have substantially the same structure, features, and characteristics as the vertical frame members 25 comprising the overlay 20 illustrated and described above in connection with FIG. 1 and FIG. 2. Further, the membrane portions 121*a*, 121*c*, 122*a*, 122*c*, 123*a*, 123*c*, 124*a*, 124*c* are each constructed of a material that may be supported away from the wound by the frame portions 121*b*, 122*b*, 123*b*, 124*b* or vertical frame members (if any) or by any or all of the same. It should be noted, however, that the membrane portions 121*a*, 121*c*, 122*a*, 122*c*, 123*a*, 123*c*, 124*a*, 124*c* may be constructed of a flexible material, as well as a semi-rigid material or even a rigid material. In each case, the membrane portions 121*a*, 121*c*, 122*a*, 122*c*, 123*a*, 123*c*, 124*a*, 124*c* and the frame portions 121*b*, 122*b*, 123*b*, 124*b* are constructed of materials and in a manner so that the overlay 120 can be supported away from the wound even with the removal of one or more of the cup members 121, 122, 123, 124. In the various embodiments of the overlay 120, the overlay 120 and its component parts may be constructed from substantially the same materials, have the same general type of structure, and be constructed in the same general manner as the overlay 20 illustrated and described above in connection with FIG. 1 and FIG. 2. It is to be noted, however, that the membrane portions 121*a*, 121*c*, 122*a*, 122*c*, 123*a*, 123*c*, 124*a*, 124*c* have sufficient strength and rigidity at the connections between the cup members 121, 122, 123, 124 so that the cup members 121, 122, 123, 124 or any combination thereof may be supported away from the wound. In some embodiments of the overlay 120 of this second version of the present invention, as illustrated in FIG. 3 and FIG. 4, the overlay 120 may also further comprise a port 128. In these embodiments, the port 128 is adapted to be of a size and shape so that the reduced pressure supply means may be operably connected to the overlay 120 by means of the port 128. In substantially the same manner as the port 28 of the overlay 20 illustrated and described above in connection with FIG. 1 and FIG. 2, the port 128 may be positioned at any of the same locations on the overlay 120, except that the port 128 may also generally not be located in a manner that would interfere with the seal between the overlapping portions of the membrane portions 121c, 122a, 122c, 123a, 123c, 124a. In addition, in the various embodiments of the overlay 120, the port 128, as well as its cylindrical channel 128a, may have substantially the same structure, features, characteristics and operation as the port 28 and channel 28a, respectively (including the flow control means), of the overlay 20 illustrated and described above in connection with FIG. 1 and FIG. 2.

Figure 5A:
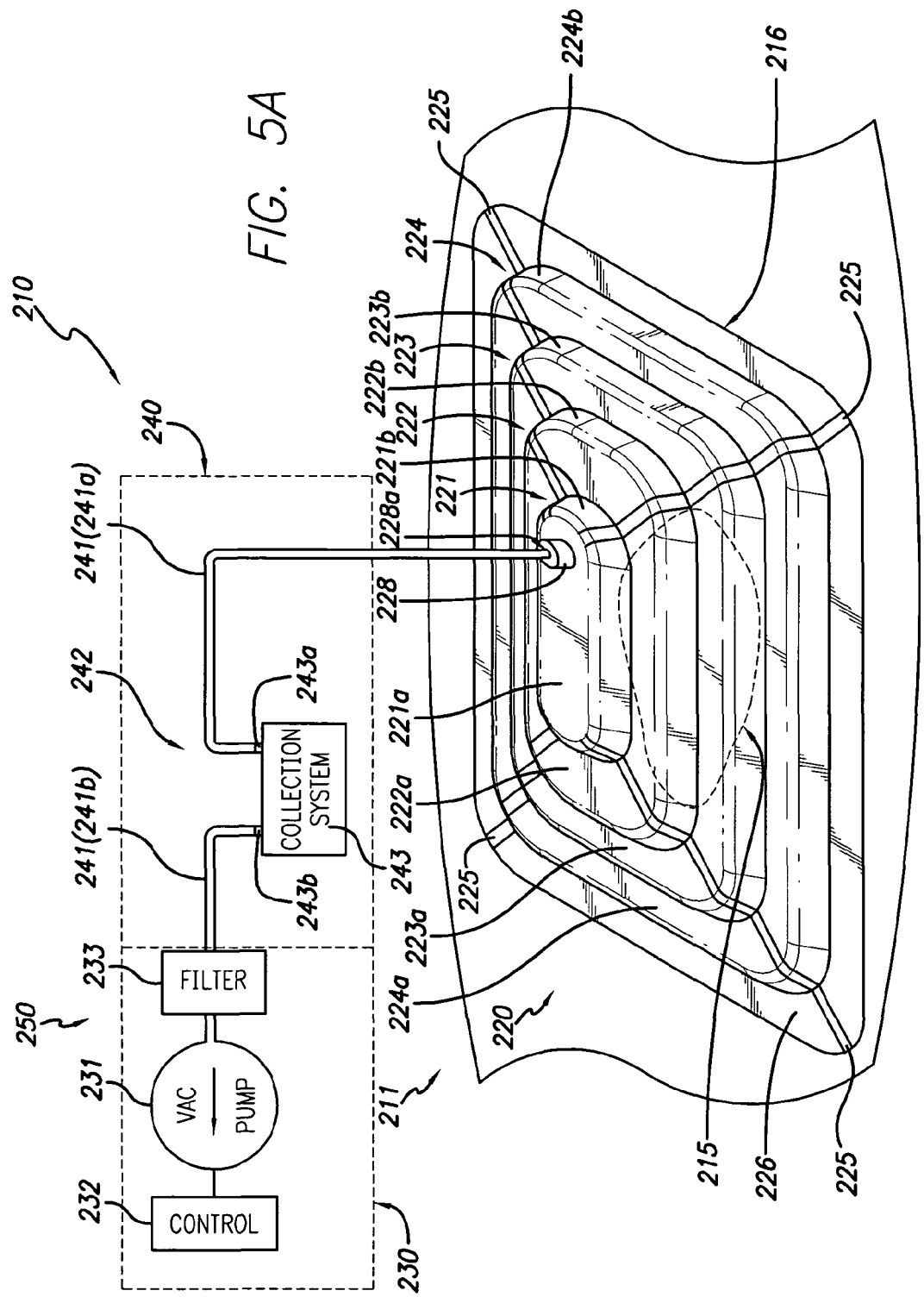
FIG. 5A is a view of an embodiment of a treatment appliance comprising the present invention, in which an embodiment of a treatment device, shown in perspective view, is placed over a wound, and in which an embodiment of a vacuum system, depicted generally and shown in schematic elevation view, provides reduced pressure within the volume under an overlay comprising the treatment device.

An embodiment of a third version of the present invention is the treatment appliance 210 illustrated in FIG. 5A. In this embodiment, the treatment appliance 210 is comprised of a treatment device 211 and a vacuum system, generally designated 250, that is operably connected to, and provides a supply of reduced pressure to, the treatment device 211. Also in this embodiment, the treatment device 211 is comprised of an overlay 220. In addition, in this embodiment, the vacuum system 250 is further comprised of a reduced pressure supply source, generally designated 230, which is illustrated schematically and described in more detail below, and reduced pressure supply means, generally designated 240, which are illustrated schematically and described in more detail below. Also in this embodiment, the reduced pressure supply means 240 are used to connect the reduced pressure supply source 230 to the overlay 220 in a manner so that reduced pressure is supplied to the volume under the overlay 220 at the site of the wound 215 to be treated, as described in more detail below. In the embodiment of the third version of the invention illustrated in FIG. 5A, the overlay 220 has substantially the same structure, features, characteristics and operation as described above and illustrated in connection with the overlay 20 of the first version of the invention illustrated and described above in connection with FIG. 1 and FIG. 2. Thus, the illustrated overlay 220 is comprised of a top cup member 221 (having a top membrane portion 221a and a top frame portion 221b), a secondary cup member 222 (having a secondary membrane portion 222a and a secondary frame portion 222b), a first additional cup member 223 (having a first additional membrane portion 223a and a first additional frame portion 223b), and a second additional cup member 224 (having a second additional membrane portion 224a and a second additional frame portion 224b). The overlay 220 is also further comprised of four vertical frame members 225. It is to be noted, however, that in other embodiments of this third version of the invention, the overlay 220 may have substantially the same structure, features, characteristics and operation as any embodiment of any of the overlays 20, 120 of the first and second versions of the invention described above and illustrated in connection with FIG. 1 through FIG. 4.

In the various embodiments of this third version of the present invention, as illustrated in FIG. 5A, the lower membrane member 226 of the overlay 220 is comprised of a flexible material and the sealing means is comprised of the suction of the lower membrane member 226 against the portion 216 of the body adjacent to the lower membrane member 226 of the overlay 220, such suction being produced by the presence of reduced pressure in the volume under the overlay 220 at the site of the wound 215. In other embodiments, the sealing means may be comprised of an adhesive, an adhesive tape, lanoline, or other sealant, or any combination of such means, that is disposed between the lower membrane member 226 and the portion 216 of the body adjacent to the lower membrane member 226 or disposed over the lower membrane member 226 and the portion of the body outside the perimeter of the lower membrane member 226. In yet other embodiments, the sealing means may be comprised of a material (not illustrated) that is positioned approximately over the overlay 220 and wrapped around the portion 216 of the body on which the overlay 220 is positioned. This material is used to hold the overlay 220 against the adjacent portion 216 of the body. For example, if the wound 260 were on the patient's leg, an elastic bandage or adhesive tape may be wrapped over the overlay 220 and around the leg.

In the embodiment illustrated in FIG. 5A, the reduced pressure supply source 230 of the vacuum system 250, which produces a source of reduced pressure or suction that is supplied to the overlay 220, is comprised of a vacuum pump 231, a control device 232, and a filter 233. Although the preferred means of producing the reduced pressure or suction is a vacuum pump 231 in this embodiment, in other embodiments of this third version of the invention other means may be used, such as an outlet port of a centralized hospital vacuum system. In the illustrated embodiment, predetermined amounts of suction or reduced pressure are produced by the vacuum pump 231. The vacuum pump 231 is preferably controlled by a control device 232, such as a switch or a timer that may be set to provide cyclic on/off operation of the vacuum pump 231 according to user-selected intervals. Alternatively, the vacuum pump 231 may be operated continuously without the use of a cyclical timer. In addition, in some embodiments the control device 232 may provide for separate control of the level of reduced pressure applied to the volume under the overlay 220 at the site of the wound 215 and the flow rate of fluid aspirated from the wound 215, if any. In these embodiments, relatively low levels of reduced pressure may be maintained at the site of the wound 215 in the volume under the treatment device 211, while still providing for the removal of a relatively large volume of exudate from the wound 215. A filter 233, such as a micropore filter, is preferably attached to the inlet of the vacuum pump 231 to prevent potentially pathogenic microbes or aerosols from contaminating, and then being vented to atmosphere by, the vacuum pump 231. In other embodiments, the filter 233 may also be a hydrophobic filter that prevents any exudate from the wound from contaminating, and then being vented to atmosphere by, the vacuum pump 231. It is to be noted that in other embodiments of the invention, the reduced pressure supply source 230 may not have a filter 233 or a control 232 or any combination of the same.

In other embodiments of the third version of the invention, the reduced pressure supply source 230 of the vacuum system 250, may be comprised of a small, portable vacuum pump 231. In some of these embodiments, a filter 233 or a power source (not illustrated), or both, may also be contained within the housing for the portable vacuum pump 231. In these embodiments, the portable vacuum pump 231 is preferably controlled by a control device 232 that is also located within the housing for the portable vacuum pump 231, which may provide substantially the same functions as the control device 232 described above. Except for its smaller size, the portable vacuum pump 231 may operate in substantially the same manner as the vacuum pump 231 described above. Also, in these embodiments, the filter 233 may have the same structure, features, characteristics and operation, and provide substantially the same functions, as the filter 233 described above. In some of these embodiments, the filter 233 may be rigidly connected to the portable vacuum pump 231. The power source may be any source of energy currently known in the art or that may be developed in the art in the future that may be used to power the portable vacuum pump 231. For example, in some embodiments, the power source may be a fuel cell, battery or connection to a standard wall electrical outlet.

In the embodiment of the third version of the invention illustrated in FIG. 5A, the reduced pressure supply means 240 of the vacuum system 250, which are used to connect the reduced pressure supply source 230 to the overlay 220 so that reduced pressure is supplied to the volume under the overlay 220 at the site of the wound 215, is comprised of at least one tubing member 241. In this embodiment, the at least one tubing member 241 is sufficiently flexible to permit movement of the at least one tubing member 241, but is sufficiently rigid to resist constriction when reduced pressure is supplied to the overlay 220 or when the location of the wound 215 is such that the patient must sit or lie upon the at least one tubing member 241 or upon the treatment device 211. In the embodiment illustrated in FIG. 5A, the at least one tubing member 241 is connected to the overlay 220 by inserting one end of the at least one tubing member 241 into an opening 228a of a port 228 of the overlay 220. In this embodiment, the at least one tubing member 241 is held in place in the opening 228a by means of an adhesive. It is to be noted that in other embodiments of this third version of the invention, the at least one tubing member 241 may be connected to the port 228 of the overlay 220 using any suitable means currently known in the art or developed in the art in the future. Examples include variable descending diameter adapters (commonly referred to as "Christmas tree" adapters), luer lock fittings and adapters, clamps, and combinations of such means. Alternatively, the port 228 and the at least one tubing member 241 may be fabricated as a single piece. Similar means may be used to connect the other end of the at least one tubing member 241 to the vacuum pump 231 or other reduced pressure supply source 230 providing the reduced pressure.

Figure 5B:
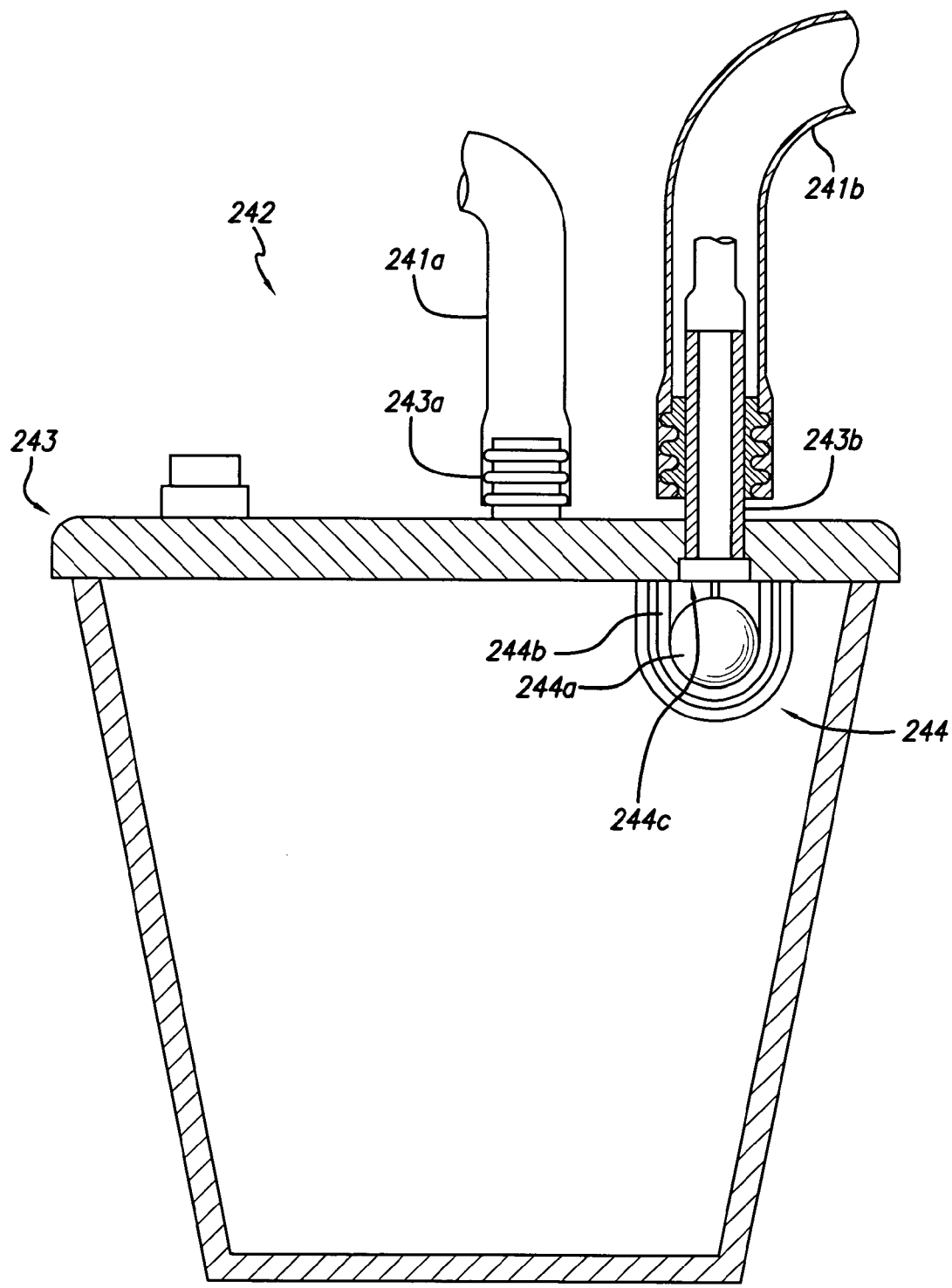
FIG. 5B is a sectional elevational detailed view of an embodiment of a collection container and the shutoff mechanism portion of the collection system of FIG. 5A.

In the embodiment illustrated in FIG. 5A, the reduced pressure supply means 240 further comprise a fluid collection system, generally designated 242, that is interconnected between the vacuum pump 231 and the overlay 220 to remove and collect any exudate that may be aspirated from the wound 215 and collected by the overlay 220. The overlay 220 functions to actively draw fluid or exudate from the wound 215. Collection of exudate in a fluid collection system 242 intermediate the pump 231 and the overlay 220 is desirable to prevent clogging of the pump 231. The fluid collection system 242 is comprised of a fluid-impermeable collection container 243 and a shutoff mechanism 244, which are described in more detail below in connection with FIG. 5B. The container 243 may be of any size and shape capable of intercepting and retaining a predetermined amount of exudate. Many examples of such containers are available in the relevant art. Referring to FIG. 5B, which is an enlarged elevational cross-sectional view of the preferred embodiment of the container 243, the container 243 includes a first port 243a at the top opening of the container 243 for sealed connection to tubing member 241a, where the other end of the tubing member 241a is connected to the overlay 220. The first port 243a enables suction to be applied to the overlay 220 through the tubing 241a and also enables exudate from the wound 215 enclosed by the overlay 220 to be drained into the container 243. The container 243 provides a means for containing and temporarily storing the collected exudate. A second port 243b is also provided on the top of the container 243 to enable the application of suction from the vacuum pump 231. The second port 243b of the collection system 242 is connected to the vacuum pump 231 by tubing member 241b. The collection system 242 is sealed generally gas-tight to enable the vacuum pump 231 to supply suction to the overlay 220 through the collection system 242.

The embodiment of the collection system 242 illustrated in FIG. 5B also includes a shutoff mechanism for halting or inhibiting the supply of reduced pressure to the overlay 220 in the event that the exudate aspirated from the wound 215 exceeds a predetermined quantity. Interrupting the application of suction to the overlay 220 is desirable to prevent exsanguination in the unlikely event a blood vessel ruptures under the overlay 220 during treatment. If, for example, a blood vessel ruptures in the vicinity of the overlay 220, a shut-off mechanism would be useful to prevent the vacuum system 250 from aspirating any significant quantity of blood from the patient. In the preferred embodiment of the shutoff mechanism 244, as illustrated in FIG. 5B, the shutoff mechanism 244 is a float valve assembly in the form of a ball 244a which is held and suspended within a cage 244b positioned below a valve seat 244c disposed within the opening at the top of the container below the second port 243b that will float upon the exudate and will be lifted against the valve seat 244c as the container 243 fills with exudate. When the ball 244a is firmly seated against the valve seat 244c, the float valve blocks the second port 243b and thereby shuts off the source of suction from the vacuum system 250. In other embodiments of the container 243, other types of mechanisms may also be employed to detect the liquid level within the container 243 in order to arrest operation of the vacuum system 250. In addition, in various embodiments of this third version of the invention, the shutoff mechanism 244 may be comprised of any means that enables the vacuum system 250 to halt the supply of reduced pressure to the overlay 220 at any time that the volume of exudate from the wound 215 exceeds a predetermined amount. Such means may include mechanical switches, electrical switches operably connected to the vacuum system controller 232, optical, thermal or weight sensors operably connected to the vacuum system controller 232, and any other means that are currently known in the relevant art or that may be developed in the relevant art in the future.

In some embodiments of this third version of the invention, the treatment appliance 211 further comprises tissue protection means (not illustrated) to protect and strengthen the surface tissue of the portions 216 of the body that are adjacent to the overlay 220. The tissue protection means protects such tissue by preventing abrasion and maceration of the tissue. Preferably, the tissue protection means is a hydrocolloid material, such as COLOPLAST Hydrocolloid 2655, anhydrous lanoline, or any combination of such hydrocolloid materials. More preferably, the tissue protection means is COLOPLAST Hydrocolloid 2655. The tissue protection means may be applied to the body tissue to be protected, or it may be applied to the surface of the overlay 220 that is to be in contact with the body tissue 216, or both, prior to placing the overlay 220 over the wound 215. It is to be noted that application of the tissue protection means to the body tissue 216 that is adjacent to the overlay 220 at the site of the wound 215 may only entail application of the tissue protection means to the parts of the body tissue 216 adjacent to the overlay 220 that require such protection.

Referring to FIG. 5A, a method of using the treatment appliance 210 of the illustrated embodiment is also disclosed. In this example, the overlay 220 is removed from an aseptic package in which it is stored. The overlay 220 is then placed over and encloses the wound 215. In some embodiments, where it is deemed necessary or desirable by the user of the appliance 210, the user may cut a portion of the overlay 220 away to reduce the size of the overlay 220 for purposes of wound 215 treatment. For example, if the user determines that a smaller overlay 220 is desirable for treatment of the wound 215, the user may use scissors to cut away the first additional cup member 223 and the second additional cup member 223 prior to placing the overlay 220 over the wound 215. Where the overlay 220 is of the type of overlay 120 illustrated and described above in connection with FIG. 3 and FIG. 4, the portions of the overlay 220 to be discarded may be removed by detaching such portions at the appropriate cup connecting means. The overlay 220 is also connected to the vacuum system 250 by means of the port 228 on the overlay 220 either before, after or during the placement of the overlay 220 over the wound 215. Where it is deemed necessary by the user of the treatment appliance 210, tissue protection means, as described above, may be placed on a portion of the overlay 220, on the body tissue to be protected, or both, prior to placing the overlay 220 over the wound 215. Reduced pressure is then supplied to the overlay 220 by the vacuum system 250. When reduced pressure is applied to the volume under the overlay 220 at the site of the wound 215, the overlay 220 is drawn downward by the reduced pressure, so that the lower membrane member 226 of the overlay 220 is drawn tightly against the surface of the adjacent portion 216 of the body, thus forming an operable seal between the lower membrane member 226 and the portion 216 of the body adjacent to the lower membrane member 226. References to an "operable seal" and "sealing means" herein refer generally to a seal that may be made gas-tight and liquid-tight for purposes of the reduced pressure treatment of the wound 215. It is to be noted that this seal need not be entirely gas-tight and liquid-tight. For example, the operable seal may allow for a relatively small degree of leakage, so that outside air may enter the volume under the overlay 220 at the site of the wound 215, as long as the degree of leakage is small enough so that the vacuum system 250 can maintain the desired degree of reduced pressure in the volume under the overlay 220 at the site of the wound 215. As another example, the operable seal formed by the overlay 220 may not be solely capable of maintaining the reduced pressure in the volume under the overlay 220 at the site of the wound 215 due to the shape of the body portion 216 at the site of the wound 215. In these cases, as well as other cases, it may be necessary to provide other sealing means (not illustrated), which are used to provide a seal between the portions of the overlay 220 and the portion 216 of the body where the operable seal is not adequate to permit reduced pressure to be maintained in the volume under the overlay 220 at the site of the wound 215. For example, in the illustrated embodiment, the sealing means may be an adhesive applied to the lower membrane member 226 of the overlay 220 or a portion of the body in a manner similar to the application of the tissue protection means described above. In other embodiments, the sealing means may be comprised of almost any suitable means to provide an adequate seal. For example, the sealing means may be comprised of an adhesive, an adhesive tape, lanoline, a stretch fabric that covers the treatment device 211 and is wrapped around a portion 216 of the body of the patient at the site of the wound 215, or any combination of such means. In the preferred embodiments of this second version of the invention, the reduced pressure maintained in the volume under the overlay 220 at the site of the wound 215 is in the range from approximately 20 mm of Hg below atmospheric pressure to approximately 125 mm of Hg below atmospheric pressure. In yet other embodiments, the reduced pressure is applied to the overlay 220 in a cyclic nature, the cyclic nature providing alternating time periods of application of reduced pressure and non-application of reduced pressure. In all of these embodiments, the reduced pressure is maintained in the volume under the overlay 220 at the site of the wound 215 until the wound 215 has progressed toward a selected stage of healing.

An embodiment of a fourth version of the invention is the treatment appliance 310 illustrated in FIG. 6. In this embodiment, the treatment appliance 310 is comprised of a treatment device 311 and a vacuum system, generally designated 350, operably connected to, and providing a supply of reduced pressure to, the treatment device 311. In addition, in this embodiment, the vacuum system 350 is further comprised of a reduced pressure supply source, generally designated 360, which is described in more detail below, and reduced pressure supply means, generally designated 340, which are described in more detail below. Also in this embodiment, the treatment device 311 is further comprised of an overlay 320, wound packing means 375, and a suction drain 345. In the embodiment of the fourth version of the invention illustrated in FIG. 6, the overlay 320 is approximately elliptical in shape, when viewed from above the overlay 320 as it is positioned over a wound 315, but otherwise generally has substantially the same structure, features, and characteristics as the embodiment of the overlay 20 illustrated and described above in connection with FIG. 6. It is to be noted, however, that in other embodiments of this fourth version of the invention, the overlay 320 may have substantially the same structure, features, characteristics and operation as any embodiment of all of the overlays 20, 120 of the first and second versions of the invention described above and illustrated in connection with FIG. 1 through FIG. 4. In the embodiment illustrated in FIG. 6, the overlay 320 is placed over and encloses a wound 315. In the illustrated embodiment, the overlay 320 may be sealed to the adjacent portions 316 of the body using any of the sealing means or operable seals described above and illustrated in connection with FIG. 5A.

In the embodiment of the fourth version of the invention illustrated in FIG. 6, the treatment device 311 is further comprised of wound packing means 375, which is placed in the area of the wound 315 under the overlay 320. In some embodiments of this fourth version of the invention, the wound packing means 375 may be placed within the wound 315 to prevent overgrowth of the tissue in the area of the wound 315. For example, and preferably in these cases, the wound packing means 375 may be comprised of absorbent dressings, antiseptic dressings, nonadherent dressings, water dressings, or combinations of such dressings. More preferably, the wound packing means 375 may be comprised of gauze or cotton or any combination of gauze and cotton. In still other embodiments of this fourth version of the invention, the wound packing means 375 may be comprised of an absorbable matrix adapted to encourage growth of the tissue in the area of the wound 315 into the matrix. In these embodiments, the absorbable matrix (as wound packing means 375) is constructed of an absorbable material that is absorbed into the epithelial and subcutaneous tissue in the wound 315 as the wound 315 heals. The matrix (as wound packing means 375) may vary in thickness and rigidity, and it may be desirable to use a spongy absorbable material for the patient's comfort if the patient must lie upon the treatment device 311 during treatment. The matrix (as wound packing means 375) may also be perforated and constructed in a sponge-type or foam-type structure to enhance gas flow and to reduce the weight of the matrix. Because of the absorbable nature of the absorbable matrix (as wound packing means 375), the matrix should require less frequent changing than other dressing types during the treatment process. In other circumstances, the matrix (as wound packing means 375) may not need to be changed at all during the treatment process. In some embodiments of this fourth version of the invention, the absorbable matrix (as wound packing means 375) may be comprised of collagens or other absorbable materials or combinations of all such materials. U.S. patent application Ser. No. 10/652,100, which was filed by one of the present inventors with the U.S. Patent and Trademark Office on Aug. 28, 2003, and is hereby incorporated by reference, also discloses various embodiments of an absorbable matrix that may be utilized with various embodiments of this fourth version of the present invention. It is to be noted, however, that wound packing means 375 may not be utilized in other embodiments of this fourth version of the invention.

In the embodiment of the fourth version of the invention illustrated in FIG. 6, the treatment device 311 is also comprised of a suction drain 345 and suction drain connection means, which are described in more detail below, to operably connect the reduced pressure supply means 340 to the suction drain 345 so that the suction drain 345 is in fluid communication with the reduced pressure supply means 340 and reduced pressure is supplied to the volume under the overlay 320 at the site of the wound 315 by means of the suction drain 345. In this embodiment, the suction drain 345 is further comprised of a bottom drain portion 345a extending into the area of the wound 315 under the overlay 320 from a top drain portion 345b positioned within the volume of the overlay and extending to connect to the reduced pressure supply means 340. In the illustrated embodiment, the top drain portion 345b is attached to a port 328 located in the overlay 320, which may be positioned on the overlay 320 in the same manner that the port 228 is located on the overlay 220, as described and illustrated above in connection with FIG. 5A. In this embodiment, the top drain portion 345b is attached to the port opening 328a on the side of the port 328 that is opposite the side of the port opening 328a that is connected to the reduced pressure supply means 340. In other embodiments, the top drain portion 345b may be permanently or removably attached to the interior surface of the opening 328a of the port 328 using any suitable means, such as an adhesive, or by the top drain portion 345b having a shape adapted so that all or a portion of it fits tightly against all or a portion of the interior surface of the opening 328a in the port 328. The suction drain system disclosed in U.S. patent application Ser. No. 11/026,733, entitled "Improved Reduced Pressure Wound Treatment Appliance," which was filed by one of the present inventors with the U.S. Patent and Trademark Office on Dec. 30, 2004, may also be used in conjunction with the present invention. The disclosure of this U.S. patent application is incorporated herein by reference. In yet other embodiments, the top drain portion 345b may be positioned between the lower membrane member 326 and the portion 316 of the body adjacent to the wound 315, so that the top drain portion 345a is directly connected to the reduced pressure supply means 340 by means of a connector 346. In these embodiments, it is to be noted that the top drain portion 345b must be sufficiently sealed against the surface of the lower membrane member 326 and the portion 316 of the body adjacent to the wound 315 in a manner so that reduced pressure can be maintained in the volume under the overlay 320 in the area of the wound 315. In the embodiment illustrated in FIG. 6, the top drain portion 345b and the bottom drain portion 345a of the suction drain 345 are comprised of polymer tubing that is flexible enough to allow the tubing to easily bend, but rigid enough to prevent the tubing from collapsing during use. In other embodiments, portions of the top drain portion 345b and the bottom drain portion 345a of the suction drain 345 may be comprised of other materials, such as flexible or semi-rigid polymers, plastics, rubber, silicone, or combinations of such materials. In yet other embodiments, the suction drain 345 may have different cross-sectional shapes, such as elliptical, square, rectangular, pentagonal, hexagonal, or other shapes. In still other embodiments, the bottom drain portion 345a of the suction drain 345 may be further comprised of wound suction means that may be used to remove debris, exudate and other matter from the wound 315. In the embodiment illustrated in FIG. 6, the wound suction means is comprised of a distal end portion 345a' of the tubing comprising the bottom drain portion 345a having a plurality of perforations 345a" in the surface of the distal end portion 345a'. In other embodiments, the distal end portion 345a' of the bottom drain portion 345a may have almost any shape or combination of shapes (e.g., circular, elliptical, square, pentagonal, or hexagonal), including a shape different from the remaining portion of the bottom drain portion 345a, may be of almost any size relative to the remaining bottom drain portion 345a (e.g., may be longer or shorter than the remaining bottom drain portion 345a or have a cross-section smaller or larger than the remaining bottom drain portion 345a, or both), may have more or fewer perforations 345a", may have different sizes and shapes of perforations 345a", may extend along different portions of the bottom drain portion 345a, and may be constructed in whole or in part of materials that are not flexible. In embodiments that have a distal end portion 345a', the distal end portion 345a' may be attached to the remaining portion of the bottom drain portion 345a in almost any manner, as long as the remaining bottom drain portion 345a is in fluid communication with the wound suction means 345a'. Examples include an adhesive in some embodiments and an adhesive tape in other embodiments. In still other embodiments, the distal end portion 345a' may be fused or welded to the remaining portion of the bottom drain portion 345a. In yet other embodiments, the distal end portion 345a' and the remaining portion of the bottom drain portion 345a may be fabricated as a single piece.

In some embodiments of this fourth version of the invention, as illustrated in FIG. 6, the top drain portion 345b may extend beyond the port 328 of the overlay 320 into the area outside the volume of the overlay 320. In some of these embodiments, as is also illustrated in FIG. 6, the suction drain connection means, which may be used to removably connect the reduced pressure supply means 340 to the top drain portion 345b of the suction drain 345 is a variable descending diameter adapter 346 (commonly referred to as a "Christmas tree" adapter) that is placed into the interior volume of the top drain portion 345b at its distal end. In other embodiments, the suction drain connection means may be clamps, fastening collars, luer lock fittings and adapters, or other fasteners or combinations thereof. In yet other embodiments, the top drain portion 345b may be fused or welded to the reduced pressure supply means 340. In still other embodiments, the top drain portion 345b and the portion of the reduced pressure supply means 340 adjacent to the top drain portion 345b may be fabricated as a single piece.

In the embodiment of this fourth version of the invention illustrated in FIG. 6, the distal end portion 345a' of the suction drain 345 extends into the interior volume of the wound packing means 375. In this embodiment, the wound packing means 375 and the suction drain 345 may be fabricated by snaking the distal end portion 345a' of the suction drain 345 through an internal passageway in the wound packing means 375, such as by pulling the distal end portion 345a' of the suction drain 345 through the passageway using forceps. Alternatively, the wound packing means 375 and the suction drain 345 may be manufactured as a single piece in sterile conditions and then be stored in an aseptic package until ready for use. In other embodiments, the distal end portion 345a' of the suction drain 345 may be placed adjacent or close to the wound packing means 375 in the area of the wound 315. The preferred means of placement of the suction drain 345 relative to the wound packing means 375 is dependent upon the type of wound 315, the type of wound packing means 375, and the type of treatment desired. Referring to FIG. 6 as an example, it is therefore to be noted that in some embodiments of this fourth version of the invention, the wound treatment device 311 may utilize a suction drain 345 without utilizing wound packing means 375, while in other embodiments a suction drain 345 may be utilized with wound packing means 375. In addition, in other embodiments of this fourth version of the invention, the wound treatment device 311 may utilize wound packing means 375 without utilizing a suction drain 345, while in other embodiments wound packing means 375 may be utilized with a suction drain 345.

In the embodiment of the fourth version of the invention illustrated in FIG. 6, the vacuum system 350 is generally comprised of a suction bulb 361 having an inlet port 362 and an outlet port 363, a bulb connection tubing member 364, an exhaust tubing member 365, an exhaust control valve 366, a filter 367, and a supplemental vacuum system (illustrated schematically and generally designated 350a). In this embodiment, the suction bulb 361 is a hollow sphere that may be used to produce a supply of reduced pressure for use with the treatment device 311. In addition, the suction bulb 361 may also be used to receive and store fluid aspirated from the wound 315. The inlet port 362 of the suction bulb 361 is connected to one end of the bulb connection tubing member 364, which is also the reduced pressure supply means 340 in this embodiment. The connection tubing member 364 is connected by suction drain connection means to the top drain portion 345b at its other end in a manner so that the interior volume of the suction bulb 361 is in fluid communication with the suction drain 345. In this embodiment, the bulb connection tubing member 364 is sufficiently flexible to permit movement of the bulb connection tubing member 364, but is sufficiently rigid to resist constriction when reduced pressure is supplied to the suction drain 345 or when the location of the wound 315 is such that the patient must sit or lie upon the bulb connection tubing member 364 or upon the treatment device 311. The outlet port 363 of the suction bulb 361 is connected to the exhaust tubing member 365. In this embodiment, the exhaust tubing member 365 is sufficiently flexible to permit movement of the exhaust tubing member 365, but is sufficiently rigid to resist constriction when reduced pressure is supplied to the suction drain 345. The inlet port 362 of the suction bulb 361 may be connected to the bulb connection tubing member 364 and the outlet port 363 of the suction bulb 361 may be connected to the exhaust tubing member 365 using any suitable means, such as by welding, fusing, adhesives, clamps, or any combination of such means. In addition, in some embodiments, which are the preferred embodiments, the suction bulb 361, the bulb connection tubing member 364, and the exhaust tubing member 365 may be fabricated as a single piece. In the illustrated embodiment, the exhaust control valve 366 and the filter 367 are operably connected to the exhaust tubing member 365. In this embodiment, the exhaust control valve 366 is used to regulate the flow of fluids (gases and liquids) to and from the suction bulb 361 and the supplemental vacuum system 350a. In embodiments of the invention that do not have a supplemental vacuum system 350a, the exhaust control valve 366 regulates flow of fluids to and from the suction bulb 361 and the outside atmosphere. Generally, the exhaust control valve 366 allows fluids to flow out of the suction bulb 361 through the outlet port 363, but not to flow in the reverse direction unless permitted by the user of the appliance 310. Any type of flow control valve may be used as the exhaust control valve 366, as long as the valve 366 is capable of operating in the anticipated environment involving reduced pressure and wound 315 exudate. Such valves are well known in the relevant art, such as sprung and unsprung flapper-type valves and disc-type valves, operating in conjunction with or without ball, gate and other similar types of valves. In this embodiment, the filter 367 is operably attached to the exhaust tubing member 365 between the outlet port 363 of the suction bulb 361 and the exhaust control valve 366. The filter 367 prevents potentially pathogenic microbes or aerosols from contaminating the exhaust control valve 366 (and supplemental vacuum system 350a), and then being vented to atmosphere. The filter 367 may be any suitable type of filter, such as a micropore filter. In other embodiments, the filter 367 may also be a hydrophobic filter that prevents any exudate from the wound 315 from contaminating the exhaust control valve 366 (and the supplemental vacuum system 350a) and then being vented to atmosphere. In still other embodiments, the filter 367 may perform both functions. It is to be noted, however, that the outlet port 363, the exhaust control valve 366, the filter 367, or any combination of the exhaust control valve 366 and the filter 367, need not be utilized in connection with the vacuum system 350 in other embodiments of the invention.

In some embodiments of the fourth version of the invention illustrated in FIG. 6 that do not utilize a supplemental vacuum system 350a, the suction bulb 361 may be used to produce a supply of reduced pressure in the following manner. First, the user of the appliance 310 appropriately seals all of the component parts of the appliance 310 in the manner described herein. For example, the overlay 320 is placed over and encloses the wound 315, as well as any other components within the volume of the overlay 320, such as the wound packing means 375 and the suction drain 345. At least a portion of the lower membrane member 326 is sealed (or placed adjacent) to the adjacent portions 316 of the body, and the suction drain 345 is connected to the bulb connection tubing member 364 by means of the connector 346. The user then opens the exhaust control valve 366 and applies force to the outside surface of the suction bulb 361, deforming it in a manner that causes its interior volume to be reduced. When the suction bulb 361 is deformed, the gas in the interior volume is expelled to atmosphere through the outlet port 363, the exhaust tubing member 365, the filter 367, and the exhaust control valve 366. The user then closes the exhaust control valve 366 and releases the force on the suction bulb 361. The suction bulb 361 then expands, drawing fluid (liquid and gas) from the area of the wound 315 under the treatment device 311 into the suction bulb 361 through the suction drain 345 and causing the pressure in such area to decrease. To release the reduced pressure, the user of the appliance 310 may open the exhaust control valve 366, allowing atmospheric air into the interior volume of the suction bulb 361. The level of reduced pressure may also be regulated by momentarily opening the exhaust control valve 366.

The suction bulb 361 may be constructed of almost any fluid impermeable flexible or semi-rigid material that is suitable for medical use and that can be readily deformed by application of pressure to the outside surface of the suction bulb 361 by users of the appliance 310 and still return to its original shape upon release of the pressure. For example, the suction bulb 361 may be constructed of rubber, neoprene, silicone, or other flexible or semi-rigid polymers, or any combination of all such materials. In addition, the suction bulb 361 may be of almost any shape, such as cubical, ellipsoidal, or polyhedral. The suction bulb 361 may also be of varying size depending upon the anticipated use of the suction bulb 361, the size of the wound treatment device 311, use of a supplemental vacuum system 350*a*, the level of reduced pressure desired, and the preference of the user of the appliance 310. In the embodiment of the invention illustrated in FIG. 6, the supplemental vacuum system 350*a* is connected to the exhaust tubing member 365 and is used to provide a supplemental supply of reduced pressure to the suction bulb 361 and treatment device 311. In this embodiment, the supplemental vacuum system 350*a* may have substantially the same structure, features, characteristics and operation of the various embodiments of the vacuum system 250 of the first version of the invention described above and illustrated in connection with FIG. 5A and FIG. 5B. It is to be noted, however, that the supplemental vacuum system 350*a* need not be used in connection with the vacuum system 350 in other embodiments of the invention.

Except as described below, the treatment appliance 310 described above and illustrated in connection with FIG. 6 may generally be used in a manner similar to the treatment appliance 210 described above and illustrated in connection with FIG. 5A and FIG. 5B. As a result, except as described below, the example of how the embodiment of the treatment appliance 210 and the overlay 220 described above and illustrated in connection FIG. 5A may be used in treatment of a wound 215 also applies to the embodiment of the appliance 310 of the fourth version of the invention described above and illustrated in connection with FIG. 6. In the case of the embodiment illustrated in FIG. 6, however, the wound packing means 375 is placed into the wound 315 and the suction drain 345 is installed prior to placement of the overlay 320 over the wound 315. In addition, the overlay 320 is placed over the wound packing means 375 and a portion of the suction drain 345. In embodiments where the distal end portion 345*a*' of a suction drain 345 is placed into the interior volume of, or adjacent to, the wound packing means 375, the distal end portion 345*a*' of the suction drain 345 is also placed in the appropriate position before the overlay 320 is placed over the wound 315. In embodiments utilizing a suction drain 345 without wound packing means 375, the suction drain 345 is installed in the overlay 320 before the overlay 320 is placed over the wound 315.

It is also to be noted that in the embodiment of the fourth version of the present invention illustrated in FIG. 6, the overlay 320 is also comprised of a pressure venting valve 380. The pressure venting valve 380 permits ambient air to enter the volume under the overlay 320 if the level of reduced pressure in the volume under the overlay 320 in the area of the wound 315 exceeds a predetermined level. For example, if the reduced pressure under the overlay 320 is not to exceed 100 mm of Hg, the pressure venting valve 380 may activate at approximately 95 mm of Hg, so that ambient air enters the overlay 320 when the set pressure level is reached. The introduction of ambient air lowers the level of reduced pressure to the desired level, at which the pressure venting valve 380 closes so that pressure may be maintained at that level. The pressure venting valve 380 may be used in conjunction any embodiment of the overlays 20, 120 illustrated and described above in connection with FIG. 1 through FIG. 4. The pressure venting valve 380 may be of any suitable type valve currently known in the relevant art or that may be developed in the relevant art in the future. For example, the pressure venting valve 380 may be a diaphragm, swing check, or other type of relief valve designed for medical use. Such valves are well known in the relevant art.

What is claimed is:

1. An apparatus for applying reduced pressure to a wound, comprising:
    an overlay comprising:
        a bottom layer made of a flexible material configured to be applied over a wound, the bottom layer being generally planar and having an upper surface and a lower surface, the lower surface comprising an adhesive, wherein the bottom layer has an elongated shape with an outer perimeter;
        a second layer made of a preformed non-planar, flexible material that is coupled with the bottom layer, the second layer having a preformed shape when coupled with the bottom layer, the second layer comprising:
            upwardly extending side walls that extend away from the upper surface of the bottom layer, and
            a generally planar upper portion that is substantially parallel to and spaced above and apart from the bottom layer to define a volume between the bottom layer, the upwardly extending side walls, and the upper portion of the second layer spaced above and apart from the bottom layer,
            wherein the generally planar upper portion of the second layer has an elongated shape having an outer perimeter that is smaller than the outer perimeter of the bottom layer;
        a port positioned nearer to a first end of the second layer than to an opposite second end of the second layer, the port configured to operably connect a reduced pressure source to the overlay through the upper portion to supply reduced pressure to the volume between the bottom layer, the upwardly extending side walls, and the upper portion of the second layer spaced above and apart from the bottom layer;
        wherein the overlay is adapted to maintain reduced pressure in the volume with the upper portion of the second layer spaced above and apart from the bottom layer; and
    a tubing member connected to the port configured to be connected with the reduced pressure source.

2. The apparatus of claim 1, further comprising foam configured to be placed between the wound and the overlay.

3. The apparatus of claim 1, further comprising the reduced pressure source, wherein the reduced pressure source comprises a vacuum pump configured to provide reduced pressure through the tubing member to the overlay.

4. The apparatus of claim 3, further comprising an exudate collection container in communication with the vacuum pump.

5. The apparatus of claim 1, wherein the tubing member is a flexible tube.

6. The apparatus of claim 1, wherein the upper portion of the second layer has a generally elliptical shape.

7. The apparatus of claim 1, wherein the port is positioned laterally off-center from a centerline of the overlay.

8. The apparatus of claim 1, wherein the upper portion of the second layer further comprises a pressure valve.

9. The apparatus of claim 1, wherein the bottom layer supports the second layer.

10. The apparatus of claim 1, wherein the upwardly extending side walls of the second layer extend generally in a direction away from a body when the overlay is applied to the wound in use.

11. The apparatus of claim 1, wherein the upper portion of the second layer is completely circumscribed by the upwardly extending side walls.

12. The apparatus of claim 1, wherein the upper portion of the second layer and the bottom layer have substantially the same shape.

13. The apparatus of claim 1, wherein the upper portion of the second layer and the upwardly extending side walls are integrally formed.

\* \* \* \* \*